United States Patent
Tajima

(10) Patent No.: US 9,796,521 B2
(45) Date of Patent: Oct. 24, 2017

(54) BELLOWS TYPE DISPENSING TIP, BELLOWS TYPE DISPENSING APPARATUS AND METHOD OF BELLOWS TYPE DISPENSING PROCESSING

(71) Applicant: Universal Bio Research Co., Ltd., Matsudo-shi, Chiba (JP)

(72) Inventor: Hideji Tajima, Matsudo (JP)

(73) Assignee: Universal Bio Research Co., Ltd., Matsudo-shi, Chiba (JP)

( * ) Notice: Subject to any disclaimer, the term of this patent is extended or adjusted under 35 U.S.C. 154(b) by 123 days.

(21) Appl. No.: 14/675,197

(22) Filed: Mar. 31, 2015

(65) Prior Publication Data

US 2015/0266658 A1    Sep. 24, 2015

Related U.S. Application Data

(63) Continuation of application No. 12/160,777, filed as application No. PCT/JP2007/050397 on Jan. 15, 2007, now Pat. No. 9,103,808.

(30) Foreign Application Priority Data

Jan. 13, 2006   (JP) ................ 2006-005870
Feb. 27, 2006   (JP) ................ 2006-051210

(51) Int. Cl.
  *B65D 83/38*  (2006.01)
  *B01L 3/02*   (2006.01)
  (Continued)

(52) U.S. Cl.
  CPC .............. *B65D 83/38* (2013.01); *B01L 3/021* (2013.01); *G01N 35/1016* (2013.01);
  (Continued)

(58) Field of Classification Search
  CPC ...... B01L 3/021; B01L 3/0275; B01L 3/0282; B01L 3/0289; B01L 9/54;
  (Continued)

(56) References Cited

U.S. PATENT DOCUMENTS 3,736,099 A    5/1973   Begg et al.
4,047,438 A    9/1977   Sekine
(Continued)

FOREIGN PATENT DOCUMENTS

EP    0520797         12/1992
JP    1-10578 Y2      3/1989
(Continued)

OTHER PUBLICATIONS

English Translation of International Search Report, International Application No. PCT/JP2007/050397, dated Mar. 6, 2007, 3 pages, International Searching Authority/Japanese Patent Office.
(Continued)

*Primary Examiner* — Jennifer Wecker
(74) *Attorney, Agent, or Firm* — Haynes and Boone, LLP

(57) ABSTRACT

There is provided a bellows type dispensing tip, a bellows type dispensing apparatus, and a method of bellows type dispensing processing that performs highly precise dispensing processing despite having a simple structure. The apparatus comprises; two or more bellows type dispensing tips having; an accommodating section that is capable of accommodating a liquid or gas in the interior thereof surrounded by a wall face, and that has a deformable deforming wall face in a portion of the wall face, and an opening section communicated with the accommodating section, through which the liquid to be suctioned/discharged can flow in and flow out due to expansion and contraction of the interior caused by deformation of the deforming wall face; and a dispensing head that supports the bellows type dispensing
(Continued)

tips, and that performs suction/discharge of the liquid into or from the bellows type dispensing tip, by deforming the deforming wall face.

10 Claims, 13 Drawing Sheets

(51) Int. Cl.
*B01L 9/00* (2006.01)
*G01N 35/10* (2006.01)
*B65D 37/00* (2006.01)

(52) U.S. Cl.
CPC ..... *G01N 35/1065* (2013.01); *G01N 35/1083* (2013.01); *B01L 3/0275* (2013.01); *B01L 3/0282* (2013.01); *B01L 3/0289* (2013.01); *B01L 9/54* (2013.01); *B01L 2400/0481* (2013.01); *G01N 35/1009* (2013.01); *G01N 35/1079* (2013.01)

(58) Field of Classification Search
CPC ........ B01L 2400/0481; G01N 35/1016; G01N 35/1065; G01N 35/1083; G01N 35/1009
See application file for complete search history.

(56) References Cited

U.S. PATENT DOCUMENTS

| | | | |
|---|---|---|---|
| 4,351,799 A | | 9/1982 | Gross et al. |
| 5,406,856 A * | | 4/1995 | Kuhn ............... B01L 3/0279 73/864.11 |
| 5,895,631 A | | 4/1999 | Tajima |
| 6,152,194 A * | | 11/2000 | Tenkanen ............... B01L 3/021 141/1 |
| 6,461,808 B1 * | | 10/2002 | Bodner ............... G01N 22/00 422/555 |
| 6,509,193 B1 | | 1/2003 | Tajima |
| 6,623,597 B1 | | 9/2003 | Taniguchi |
| 6,805,840 B1 | | 10/2004 | Tajima |
| 2003/0075556 A1 * | | 4/2003 | Tajima ............... G01N 35/1011 222/23 |
| 2003/0190263 A1 | | 10/2003 | Yiu |
| 2004/0026444 A1 | | 2/2004 | DeSilva et al. |
| 2004/0033554 A1 | | 2/2004 | Powers |
| 2004/0056048 A1 | | 3/2004 | Kaartinen |
| 2004/0067170 A1 * | | 4/2004 | Higuchi ............... B01L 3/0279 422/511 |
| 2006/0034732 A1 | | 2/2006 | Bar |
| 2008/0078258 A1 * | | 4/2008 | Price ............... B01L 3/0279 73/864.01 |

FOREIGN PATENT DOCUMENTS

| | | |
|---|---|---|
| JP | 3068347 B | 10/1991 |
| JP | 5256859 | 10/1993 |
| JP | 11-242033 | 9/1999 |
| JP | 2001183382 A | 7/2001 |
| JP | 3630493 | 3/2005 |
| JP | 3682302 | 8/2005 |
| WO | WO 9815800 | 4/1998 |
| WO | WO9947267 A1 | 9/1999 |

OTHER PUBLICATIONS

English Translation of International Preliminary Report on Patentability, Chapter II, International Application No. PCT/JP2007/050397; 4 pages, International Preliminary Examination Authority/Japanese Patent Office.
Written Opinion in International Application No. PCT/JP2007/050397; Feb. 23, 2007; 3 pages; International Searching Authority/Japanese Patent Office.
Notice of Allowance regarding U.S. Appl. No. 12/160,777 dated Jan. 13, 2015 (11 pages).
Non-Final Office Action regarding U.S. Appl. No. 12/160,777 dated Jun. 24, 2014 (18 pages).
Final Office Action regarding U.S. Appl. No. 12/160,777 dated Mar. 21, 2013 (16 pages).
Non-Final Office Action regarding U.S. Appl. No. 12/160,777 dated Jun. 21, 2012 (20 pages).
Requirement for Restriction/Election regarding U.S. Appl. No. 12/160,777 dated Mar. 14, 2012 (6 pages).

* cited by examiner (a)

(b)

BELLOWS TYPE DISPENSING TIP, BELLOWS TYPE DISPENSING APPARATUS AND METHOD OF BELLOWS TYPE DISPENSING PROCESSING

CROSS REFERENCE

This application is a continuation of U.S. patent application Ser. No. 12/160,777, which is a United States national phase application of international patent application number PCT/JP2007/050397, filed Jan. 15, 2007, which claims priority to Japanese patent application No. 2006-051210, filed Feb. 27, 2006, and Japanese patent application No. 2006-005870, filed Jan. 13, 2006, the disclosures of which are incorporated herein by reference.

TECHNICAL FIELD

The present invention relates to a bellows type dispensing tip, a bellows type dispensing apparatus, and a method of bellows type dispensing processing.

BACKGROUND ART

Heretofore there is known a patented dispensing apparatus, the patent application of which was filed by the applicant of the present patent application. In this dispensing apparatus a dispensing tip is fitted and attached to a dispensing tip attachment opening in a bottom end section of a nozzle, and a plunger within a cylinder that communicates with the nozzle is slid, to thereby suction or discharge a liquid into the dispensing tip through the bottom end thereof (Patent Document 1 to Patent Document 4).

However, the mechanisms of the cylinder, the plunger, and the like, used in the above dispensing apparatus are components manufactured at a high level of precision such as an injection syringe. In particular, variation in the inner capacity of the cylinder basically corresponds to variation in the inner capacity of the dispensing tip, and it is necessary to transmit such that there is no looseness in the joining section between the plunger and the driving apparatus of the plunger. Moreover, the suctioning/discharging mechanism and the dispensing tip are fitted together so that there is no leakage of gas or liquid. Consequently, there is concern that a high level of product quality management is needed. Furthermore, there is a problem in that since a cylinder with a capacity corresponding to the capacity of the dispensing tip is needed to control suction and discharge of the dispensing tip, a larger apparatus is needed in order to cope with liquid of a large volume.

On the other hand, heretofore there is known a dropper that is capable of accommodating liquid or gas in the interior thereof surrounded by wall faces made of rubber or the like, and that suctions or discharges the liquid when the wall faces are deformed by manually pressing. However, since this dropper is operated manually, a single user can only operate one dropper, and consequently simultaneous processing cannot be performed using a number of droppers. Moreover, since deformation in the dropper differs depending on the magnitude of the operating force, the direction of the force, and the position where the force is applied, it is difficult with manual operation of the dropper to perform quantitively precise processing, and repeat such processing at a high level of reproducibility.

As a remedial measure, there is a method of performing direct transfer from container to container without use of a dispensing tip. However, while this method simplifies the structure of the apparatus, a sufficient number of operators are required. Moreover there is a problem of the possibility of contamination due to container to container contact, so that reliability is not high.

Patent Document 1: Japanese Patent No. 3115501
Patent Document 2: Japanese Patent No. 3739953
Patent Document 3: Japanese Patent No. 3630493
Patent Document 4: Japanese Patent No. 3682302

DISCLOSURE OF THE INVENTION

Problems to be Solved by the Invention

Consequently, in order to solve the above problems, a first object of the present invention is to provided a bellows type dispensing tip, a bellows type dispensing apparatus, and a method of bellows type dispensing processing that are highly precise despite their simple and compact structure, and that are capable of handling liquid in various volumes (from approximately several $\mu$ liters to approximately several 10 milliliters), and efficiently performing processing. A second object of the present invention is to provide a bellows type dispensing tip, a bellows type dispensing apparatus, and a method of bellows type dispensing processing that do not require a high level of precision for water-tightness, air-tightness, and the like in manufacturing and product quality management, and that can be inexpensively provided, reduce management load, and reliably prevent cross contamination. A third object of the present invention is to provide a bellows type dispensing tip, a bellows type dispensing apparatus, and a method of bellows type dispensing processing capable of consistently automating various kinds of complex processings.

Means for Solving the Problems

A first aspect of the present invention is a bellows type dispensing apparatus comprising: one or two or more bellows type dispensing tips having; an accommodating section that is capable of accommodating a liquid or gas in the interior thereof surrounded by a wall face, and that has a deforming wall face in a portion of the wall face capable of predetermined deformation without practically changing an entire surface area of the wall face, and an opening section communicated with the accommodating section, through which a liquid to be suctioned/discharged can flow in/flow out in due to expansion and contraction of the interior caused by deformation of the deforming wall face; and a dispensing head that supports one or GHCVB/ASDFGH1 two or more of the bellows type dispensing tips so that the opening section does not move due to deformation of the deforming wall face, and that performs suction/discharge of the liquid into or from the bellows type dispensing tip at once, by deforming the deforming wall face of the bellows type dispensing tip at once.

Here, the "deforming wall face" refers to a flexible wall face capable of being deformed, and for which the surface area of the deforming wall face does not change due to the deformation. Therefore, in a wall face having the deforming wall face incorporated therein, the entire surface area does not change due to the deformation. "A portion of the wall face" refers, for example, to a wall face portion of the entire wall face of the accommodating section excluding a portion in close proximity to the opening section, and between the wall face portion and the opening section there is provided a non-deforming wall face that does not deform.

Moreover, it is preferable that the "predetermined deformation" of the deforming wall face be a deformation that practically sets an internal capacity according to the degree of deformation to be applied. That is to say, it is preferable that the interior surrounded by the wall face expand or contract according to the degree that the deforming wall face is pushed or pulled, or that the force is removed, along a certain deformation direction, thereby uniformly setting the capacity of the interior.

The deforming wall face may be biased in the direction of expansion or contraction of the interior due to the deformation. If the deforming wall face is biased in the expanding direction, it is contracted by applying a force in the direction opposite to that of the expansion, and is deformed in the expanding direction by removing the force. If the deforming wall face is biased in the contracting direction, it is expanded by applying a force in the direction opposite to that of the contraction, and is deformed in the contracting direction by removing the force. The deforming wall face refers to a wall face having a bellows formed therein, or a wall face that is formed with an elastic sheet member or film member such as rubber, or that is formed with a flexible sheet member or film member such as a wall face having a built-in spring with an elastic force in the deforming direction.

The "suction/discharge" refers to suctioning and/or discharging. The material of the bellows type dispensing tip is a resin such as polyethylene resin, polypropylene resin, polyester resin, polystyrene resin, polyvinyl resin, and acrylic resin, an elastic body such as rubber, an other type of flexible material, or a combination of these materials. It is preferable that the bellows type dispensing tip be transparent or semi-transparent.

"The bellows type dispensing tip is supported so that the opening section does not move due to deformation of the deforming wall face" means that the bellows type dispensing tip is attached to the dispensing head so that the position and the shape of the opening section does not practically change due to deformation of the deforming wall face. This is because, unlike the case of a cylinder type dispensing tip having a separately formed plunger and opening section that slide when performing a suction/discharge, in this bellows type dispensing tip, the deforming wall face that deforms when performing a suction/discharge, and the opening section, are provided as continuous members. For example, the supporting position of the tip such as the position of the tip to be attached or fixed to the dispensing head is in the non-deforming wall face that does not deform, other than the deforming wall face, provided between the opening section and the deforming wall face so as not to deform. It is preferable that the opening section is supported so as to face downward.

The size of the bellows type dispensing tip is, for example, such that the length along the opening section through to the attachment opening section, or in the axial direction is from several centimeters to several tens of centimeters, and the capacity thereof is for example from several micro-liters to several tens of milliliters, depending on the above length. The amount of suction/discharge is, for example, approximately from several micro-liters to several tens of milliliters, depending on the capacity.

A second aspect of the present invention is a bellows type dispensing apparatus further comprising a container set having a plurality of containers capable of accommodating various kinds of liquid solutions, and a head moving section that relatively moves the dispensing head with respect to the container set, and the opening section can be inserted into the container at once. In this case, if the opening section is supported so as to face downward, a suction, discharge, and transfer of a liquid can be smoothly performed. "Liquid solutions" include liquids containing various kinds of reagents, specimens, chemical substances, or magnetic materials. "Container" includes a container provided with a plurality of liquid accommodating sections, each of which is provided in a position corresponding to the opening section.

A third aspect of the present invention is a bellows type dispensing apparatus wherein the dispensing head has; a tip supporting section capable of supporting two or more of the bellows type dispensing tips, and a movable mechanism that deforms the deforming wall face of the bellows type dispensing tip at once with use of a movable member capable of forward/backward operation at once along a deforming direction of the deforming wall face.

The movable member deforms the deforming wall face by performing forward/backward movements in a state of being in contact with, being in contact with and separated from, or being connected to the accommodating section. In order to support the bellows type dispensing tip, it is preferable in the view of process control that the bellows type dispensing tip is supported so as to prevent movement against the forces in two directions, namely the internal expanding direction and contracting direction, applied by the movable member, so that the portion of the bellows type dispensing tip other than the deforming wall face, particularly the position of the opening section, does not move due to the deformation. This is because, in the case of the bellows type dispensing tip, the deformation wall face and the other portions are integrated or connected continuously. In order for this to be realized, the bellows type dispensing tip is supported so as to be sandwiched along the deformable direction. For example, if the deformation direction is in the vertical direction, it is preferable that the bellows type dispensing tip or one portion thereof be supported while being sandwiched from above and below.

A fourth aspect of the present invention is a bellows type dispensing apparatus, wherein the dispensing head or the container set has a magnetic device capable exerting or removing a magnetic field on or from the interior of the accommodating section or the container. Consequently, when suctioning or discharging a suspension containing a number of magnetic materials that hold biological compounds such as; a protein, a peptide, an amino acid, DNA, RNA, an oligonucleotide, and a sugar chain, into or from the bellows type dispensing tip, or when storing such suspension in the bellows type dispensing tip, it is possible to exert a magnetic field on the interior of the tip so as to attach the magnetic materials to the inner wall of the tip, and separate the magnetic materials, and hence the biological compounds.

A fifth aspect of the present invention is a bellows type dispensing apparatus having a control section that controls deformation of the deforming wall face and/or movement between the dispensing head and the container set, based on the number or structure of the bellows type dispensing tip, a liquid to be suctioned/discharged, a substance contained in the liquid, an amount, an accommodating position, a temperature or concentration of the liquid, processing contents, or instructions. The above substance includes biological materials such as nucleic acid, proteins, sugar chains, and amino acids, as well as various kinds of chemical substances including metallic materials. Moreover, "liquid" includes a solution and suspension. The suspension includes, for example, a suspension of a magnetic material capable of bonding with various kinds of substances by a reaction, or that is bonded by a reaction.

A sixth aspect of the present invention is a bellows type dispensing apparatus wherein a predetermined reference position for deformation of the deforming wall face is set, and control of deformation of the deforming wall face is performed with the reference position as a reference.

Here, the "predetermined reference position" is determined according to factors including the amount of a liquid to be handled in processing, the capacity of the bellows type dispensing tip to be used, the processing contents, and the finishing precision of the bellows type dispensing tip.

For example, in the case where the amount of liquid to be handled in processing is very small (for example, in the case of an order from several µ liters to several 100µ liters), and the capacity of the bellows type dispensing tip to be used is small, if the processing requires a high level of precision, or if the level of finishing precision of the bellows type dispensing tip is not high, then as a reference position, a position along the deformation direction of the movable member or the deforming wall face in a condition with the bellows type dispensing tip already subjected to a predetermined deformation, is made a reference. Accordingly, the control can be performed at a high level of precision. In this case, for example, it is preferable to set so that all of a predetermined maximum suction amount of the liquid that flows into the dispensing tip due to a predetermined maximum deformation amount can be discharged. As a result, it is possible to prevent the liquid from being left inside the bellows type dispensing tip when discharging liquid from the bellows type dispensing tip.

For example, in the case where, with the predetermined internal capacity of the bellows type dispensing tip as V0, and taking the position of the movable member or the deforming wall face corresponding to this state as a reference, the predetermined maximum internal capacity due to deformation of the bellows type dispensing tip is V1, and the predetermined minimum internal capacity due to deformation of the bellows type dispensing tip is V2 (V1>V0>V2), then it is preferable to set the reference position so as to give a relationship where the predetermined maximum suction amount of the liquid that flows into the dispensing tip (V1−V0) is smaller than the predetermined maximum amount (V0−V2), that is, V1−V0≤V0−V2, that is, (V1+V2)/2≤V0).

Here, since the maximum deformation amount is a "predetermined maximum deformation amount", it does not have to be a physically maximum amount. Since "the entire maximum suction amount can be discharged", the "maximum discharge amount" needs to be an amount greater than or equal to the "maximum suction amount". As a result, processing can be performed without worrying about the remaining amount of the liquid inside the bellows type dispensing tip.

On the other hand, if the amount of liquid to be handled is large (for example, in the order of several milliliters), or if the processing does not require a very high level of precision, it is possible to perform control with a position of a non-deforming state where the bellows type dispensing tip is not deformed as a reference. Such a case refers to the case where, for example, in a state where the movable member has not come into contact with the bellows type dispensing tip, a position along the deformation direction (for example, a position 1 millimeter away from the tip) is taken as the reference position.

A seventh aspect of the present invention is a bellows type dispensing apparatus wherein a bellows is formed in the deforming wall face.

Here, the "bellows" refers to a sheet member or a film member formed with waves or folds having peaks and valleys formed along a crosswise direction substantially perpendicular to a predetermined deformation direction, and that can bend at the peaks and valleys. In the case where the sheet or film member formed with the bellows is used for the cylindrical shaped surrounding wall face having its axis in the deformation direction, the shape of the waves or folds comprises a circumferential shaped or closed curved line shaped (a curved line also includes a straight line) peaks and valleys included in a straight line perpendicular to the deformation direction, or in a plane perpendicular to the deformation direction.

The bellows is formed for example, so that the entire wall face of the accommodating section is separated into two across the deformation direction of the bellows. Therefore, the deformation direction substantially matches the normal line direction of each plane that includes each of the peaks and valleys of the waves or folds of the bellows.

An eighth aspect of the present invention is a bellows type dispensing apparatus wherein the opening section is provided at a bottom end of the bellows type dispensing tip, the accommodating section is provided above the opening section, the deforming wall face capable of deforming in the vertical direction, is provided in one portion of the wall face that surrounds the accommodating section so as to separate the inner wall face into an upper and lower portion, and a top end of the accommodating section, and the movable member can be brought in contact with each other or connected to each other.

A ninth aspect of the present invention is a bellows type dispensing apparatus wherein the accommodating section has: a deforming section capable of accommodating a gas, that can be brought in contact with or connected to the movable member, and that has a deforming wall face that can be deformed by the movable member; and a non-deforming section capable of accumulating a liquid, that communicates with the deforming section, that is formed with a non-deforming wall face that does not deform, and that has an opening section on a tip end thereof.

A tenth aspect of the present invention is a bellows type dispensing apparatus wherein the dispensing head or the container set has a tip arrangement holding section that can detachably hold a plurality of the bellows type dispensing tips arranged in a line arrangement or in a plane arrangement at predetermined intervals. The "plane" arrangement, for example, includes a grid arrangement, a circumferential arrangement, and a multiple concentric circle arrangement.

The "grid" arrangement has a column direction and a row direction, however these two directions do not necessarily have to be orthogonal to each other. A single column arrangement and a single row arrangement are also special grid arrangements. The "predetermined intervals" are given intervals so as to correspond to the liquid accommodating section of each container provided in the container set. There may be prepared the tip arrangement holding section having various types of pitches and numbers, according to the number, types, and amount of the liquid solutions to be handled.

An eleventh aspect of the present invention is a bellows type dispensing apparatus wherein the tip supporting section of the dispensing head supports a plurality of the bellows type dispensing tips by attaching a tip arrangement holding section that can detachably hold a plurality of the bellows type dispensing tips arranged in a line arrangement or in a plane arrangement at predetermined intervals, while allowing each bellows type dispensing tip to deform. In order to allow this deformation, for example, the tip arrangement holding section needs to be attached in a position that enables the movable member of the dispensing head to deform the deforming section of the bellows type dispensing tip.

A twelfth aspect of the present invention is a bellows type dispensing apparatus wherein: the bellows type dispensing tip has the opening section and the accommodating section; the accommodating section has a deforming section capable of accommodating a gas, that can be brought in contact with or connected to the movable member, and that has a deforming wall face that can be deformed by the movable member; and a non-deforming section capable of accumulating a liquid, that communicates with the deforming section, that is formed with a non-deforming wall face that does not deform, and that has the opening section on a tip end thereof. The tip arrangement holding section has a plate provided with a plurality of through holes in a line or plane arrangement and pierced at predetermined intervals; each of the bellows type dispensing tips is inserted into and held in each of the through holes; the opening section of the bellows type dispensing tip is inserted through the through hole to be brought below the plate; and the deforming section of the accommodating section is held so as to be brought above the plate.

A thirteenth aspect of the present invention is a bellows type dispensing apparatus wherein the bellows type dispensing tip has an interior detection region, and in the dispensing head there is provided a light detection section for detecting a state of the interior, through the interior detection region. Therefore, the interior detection region is provided such that when the interior detection region of the bellows type dispensing tip is present below the plate, the light detection section is also present below the plate. Here, the "interior detection region" is such that the side face thereof is formed in a plane face rather than a curved face so as to enable irradiation and transmission of light into the interior to be performed easily, thereby preventing diffused reflection of the light and prevent the occurrence of a bend or the like in the tip. For example, the "state of the interior" on a plane face includes the presence of a liquid and the presence of a liquid level. Here, the "interior detection region" refers to a region in the bellows type dispensing tip formed to attain a transmissivity of light greater than that of the surrounding region.

A fourteenth aspect of the present invention is a bellows type dispensing apparatus wherein the tip arrangement holding section is provided with a plurality of loose insertion sections for loosely inserting and holding the bellows type dispensing tip therein, for each of the respective bellows type dispensing tips to be held. Examples of the loose insertion sections include a cylinder, a plurality of rods, nets, and tubes, formed so as to surround the bellows type dispensing tips.

A fifteenth aspect of the present invention is a bellows type dispensing apparatus wherein the magnetic device has a plurality of magnets provided so as to be able to come into contact with and separate from each accommodating section of one or more of the bellows type dispensing tips at once.

For example, in the case where the dispensing head has the tip supporting section, and the tip supporting section supports a plurality of the bellows type dispensing tips by attaching the tip arrangement holding section capable of detachably holding a plurality of the bellows type dispensing tips arranged in a grid at predetermined intervals while allowing the respective bellows type dispensing tips to deform, the magnetic device has: at least (number of columns−1) or (number of rows−1) of comb teeth members that are provided so as to be able to relatively move in the column direction or row direction of the bellows type dispensing tips that can be arranged in the grid, and that are provided extending along the column direction or the row direction and provided corresponding to the predetermined intervals and with a width that respectively enables insertion of the dispensing tips in between the columns or rows; and a supporting member that connects to one end side of each comb teeth member, and each comb teeth member is provided with magnets, as many as the number of the columns or rows, arranged at the predetermined intervals in positions corresponding to the respective bellows type dispensing tips. In the case of exerting a magnetic field on the bellows type dispensing tips, all of the magnets may be moved so as to be brought to positions with shortest distances from all of the respective bellows type dispensing tips, and in the case of removing the magnetic field, all of the magnets may be completely evacuated from the tip arrangement holding section in which the bellows type dispensing tips are arranged, or the respective magnets may be moved to intermediate positions of the predetermined intervals of the bellows type dispensing tips.

A sixteenth aspect of the present invention is a bellows type dispensing tip comprising: an accommodating section that is capable of accommodating a liquid or gas in the interior thereof surrounded by a wall face and that has a deforming wall face in one portion of the wall face, capable of predetermined deformation without practically changing a total internal surface area of the wall face; and an opening section that is communicated with the accommodating section and that enables inflow/outflow of a liquid suctioned/discharged by expansion and contraction of the interior caused by deformation of the deforming wall face, wherein: the opening section is provided at a bottom end of the bellows type dispensing tip; the deforming wall face is formed in one portion of the wall face surrounding the accommodating section so as to be able to deform in the vertical direction; and the accommodating section has; a deforming section capable of accommodating a gas, that is provided above the opening section, and that has the deforming wall face, and a non-deforming section capable of accumulating a liquid, that communicates with the deforming section, that does not have the deforming wall face, and that has the opening section on a tip end.

Here, the accommodating section is, for example, formed with the above mentioned resin, and the deforming wall face is, for example, such that the deforming section provided with the bellows is formed by means of blow molding, and the non-deforming section is formed by means of injection molding. Alternatively, both of the deforming section and the non-deforming section are found by means of blow molding. The "deforming wall face" is as described in the first aspect of the present invention.

A seventeenth aspect of the present invention is a bellows type dispensing tip wherein the non-deforming section has: a thick tube section that communicates with the deforming section; a thin tube section having the opening section; and a transitional section formed between the thick tube section and the thin tube section.

Here, the shape of the "transitional section" is, for example, formed in a conical shape, a funnel shape, or a step shape. Moreover, the shape of the thick tube section and the thin tube section is not limited to a cylindrical shape, and it may be a rectangular column shape, a polygonal shape, a conical shape, a prismoid shape, or a polygonal prismoid shape.

Furthermore, it is possible, with the tip end of the thin tube section formed in a tapered or sharp shape, to pierce the film of a pre-packed type reagent accommodating container, the opening section of which is coated with the film, pre-accommodating a liquid solution that contains a reagent or specimen therein, to thereby suction the liquid accommodated within the container through the thin tube section.

An eighteenth aspect of the present invention is a bellows type dispensing tip, wherein the thick tube section, the deforming section, and the transitional section are integrally formed, and a top end section of the thin tube section is attached to a bottom end section of the transitional section.

Here, the tip end section of the thin tube section is, for example, fitted to the bottom end section of the transitional section, and is attached using an adhesive, thermal welding, ultrasonic welding, or the like. Therefore, the material that may be used for the thin tube section includes a material, such as a metallic material, polypropylene, and polystyrene, that is harder than the soft material for forming the portion containing the deforming section, such as polyethylene and polyester. The portion other than the thin tube section, that is, the portion in which the thick tube section, the deforming section and the transitional section are integrally formed, may be formed by blow molding, and the thin tube section may be formed by injection molding.

A nineteenth aspect of the present invention is a bellows type dispensing tip, further having a holder for loose insertion and holding of the accommodating section, and the holder has an upper side opening section provided on an upper side thereof and a lower side opening section that enables the opening section to be externally exposed.

Moreover, the holder may be such that in order to allow the bellows type dispensing tip to come into contact with or be connected with the movable member in a state of being loosely inserted in the holder, the movable member is inserted through the upper side opening section or through a slit provided in the side face of the holder, so as to be in contact with or be connected with the accommodating section.

Here, the lower side opening section is preferably, for example, provided so as to allow the thin tube section to project.

A twentieth aspect of the present invention is a bellows type dispensing tip, wherein the non-deforming section is provided with an interior detection region interposed between transparent flat plate side faces parallel with each other.

A twenty-first aspect of the present invention is a method of bellows type dispensing processing comprising: a supporting step for supporting a plurality of bellows type dispensing tips having; an accommodating section that is capable of accommodating a liquid or gas in the interior thereof surrounded by a wall face, and that has a deforming wall face in a portion of the wall face, capable of a predetermined deformation without practically changing an entire surface area of the wall face, and an opening section communicated with the accommodating section, through which liquid to be suctioned/discharged can flow in and flow out due to expansion and contraction of the interior caused by deformation of the deforming wall face, on a dispensing head so that the opening section does not move due to deformation of the deforming wall face; a moving step for moving the dispensing head; and a deforming step for inserting the opening section into a container and deforming the deforming wall face at once.

Here, in the deforming step, it is preferable to detect a state of the interior of the bellows type dispensing tip, and detect the presence of the liquid inside the tip and a liquid level, to thereby detect whether or not an instructed processing is being performed.

A twenty-second aspect of the present invention is a method of bellows type dispensing processing, wherein the supporting step is performed by attaching a tip arrangement holding section capable of detachably holding a plurality of the bellows type dispensing tips arranged in a line or in a plane face at predetermined intervals, to the dispensing head while allowing each of the bellows type dispensing tips to deform.

A twenty-third aspect of the present invention is a method of bellows type dispensing processing, wherein the deforming step sets a predetermined reference position along the deforming direction in which the deforming wall face is deformed, and deforms the deforming wall face, taking the above reference position as a reference. The example of the "predetermined reference position" has been described in the sixth aspect of the present invention.

A twenty-fourth aspect of the present invention is a method of bellows type dispensing processing, wherein: the above opening section is provided at a bottom end of the bellows type dispensing tip; the deforming wall face is provided in a portion of a wall face surrounding the accommodating section so as to be able to deform in the vertical direction; the accommodating section has; a deforming section capable of accommodating a gas, that is provided above the opening section, and that has the deforming wall face, and a non-deforming section capable of accumulating a liquid, that communicates with the deforming section, that does not have the deforming wall face, and that has the opening section; and the deforming step has a step for contacting or connecting a movable member with or to a top end face of the accommodating section, and a step for lowering and/or raising the movable member.

A twenty-fifth aspect of the present invention is a method of bellows type dispensing processing, wherein raising and lowering of the movable member is performed by setting a predetermined reference position along the vertical direction in which the deforming wall face is deformed, and then using the reference position as a reference. The example of the "predetermined reference position" has been described in the sixth aspect of the present invention.

A twenty-sixth aspect of the present invention is a method of bellows type dispensing processing, wherein in the above liquid, a magnetic material that can bond with a predetermined substance or that has been bonded with a predetermined substance is suspended, and the magnetic material is attached to an inner wall of the accommodating section or the container and separated, by exerting a magnetic field on the accommodating section or a container of the container set. In order to place a particular emphasis on a case of having two or more of the bellows type dispensing tips, the bellows type dispensing apparatus may also be called a bellows type integrated processing apparatus, and the method of bellows type dispensing processing may also be called a method of bellows type integrated processing.

Effects of the Invention

According to the first, sixteenth, and twenty-first aspects of the present invention, by mechanically deforming the deforming wall face, the liquid can be suctioned and discharged. Therefore, without use of a fluid dynamic system, for example, a complex tube passage such as a cylinder for streaming a liquid or gas, it is possible to perform dispensing processing while reducing the size of the apparatus and simplifying the structure of the apparatus. As a result, it is possible to perform manufacturing inexpensively and easily. Moreover, since use of a cylinder or the like is not required, it is possible to handle a liquid of a large volume, despite the compact size of the apparatus.

Furthermore, since processing of a liquid such as suctioning and discharging is performed by deforming the deforming wall face without changing the total inner surface area of the wall face, the members constituting the wall face do not have to be fitted with or slid on each other. As a result, without the need of a high level of finishing precision for fitting or sliding these members, perfect water-tightness and air-tightness can be attained, cross contamination can be reliably prevented, and highly reliable dispensing processing can be performed. Moreover, since suctioning/discharging can be performed without use of a cylinder, it is possible to handle liquid of a large volume, despite the compact size of the apparatus.

Furthermore, the bellows type dispensing tip is supported so as to prevent the movement of the opening section caused by a force applied for deforming the deforming wall face. Moreover a plurality of the bellows type dispensing tips can be deformed all at once under the same conditions. Therefore it is possible to perform precise position control and highly reproducible suctioning/discharging control, even with use of the bellows type dispensing tips. Moreover, even with use of the bellows type dispensing tips, a number of processings can be parallelly performed to achieve a high level of efficiency, and even in the case where a number of containers are closely arranged, highly reliable processing can be performed.

According to the second aspect of the present invention, by pre-accommodating a required reagent in the container, it is possible to easily automate dispensing processing.

According to the third aspect of the present invention, with only use of a mechanical mechanism, which does not come in contact with a processing subject gas/liquid, for moving the movable member along the deforming direction, it is possible to perform liquid processing such as suctioning, discharging, transferring or the like. Therefore the portion that can come into contact with the liquid is substantially limited to the container and a closed space within the tip, and accordingly contamination can be reliably prevented.

According to the fourth and twenty-sixth aspects of the present invention, since a magnetic field is exerted on and removed from the interior of the accommodating section or the container, by attaching the magnetic material in the liquid containing a magnetic material suspension to the inner wall and thus separating, it is possible to consistently automate the processing including the separation processing.

According to the fifth aspect of the present invention, the deformation of the deforming wall face and/or the movement of the dispensing head is controlled based on the structure of the bellows type dispensing tip, and therefore suctioning/discharging can be reliably performed.

According to the sixth, twenty-third, and twenty-fifth aspects of the invention, control of deformation is performed based on a reference position at which at least either an internal expansion or a contraction caused by the wall face deformation is possible. Therefore for example, in the case where an internal expansion and contraction due to the deformation are both possible, it is possible to immediately address both expansion and contraction, and a quick and efficient processing can be performed. In this case, the deformation is often constant, and therefore a highly precise control can be performed. Moreover, by appropriately setting the reference position, it is possible to prevent the liquid from being left inside the bellows type dispensing tip when discharging the liquid.

According to the seventh aspect of the present invention, a bellows is formed as the deforming wall face. Therefore a wall face having a high deforming rate can be formed with a simple construction. Moreover, since the bellows can be formed with a rigid member, it is highly resistant to damage. Furthermore, there are defined a constant position and direction at and in which a bend is formed by deformation, and therefore the deformation is highly regular and the pattern of deformation is highly constant.

According to the eighth and twenty-fourth aspects of the present invention, the deformation can be performed by bringing the movable member in contact with or connecting it with the top end of the accommodating section, and therefore the structure of the bellows type dispensing apparatus is simple while providing ease of use. Moreover, since the deformation direction is provided in the vertical direction, it is possible to ensure a large difference in the internal capacity of the accommodating section between the state of the deforming wall face being deformed for the maximum internal capacity and the state of the deforming wall face being deformed for the minimum internal capacity, without increasing the diameter or the horizontal cross-section area. As a result, an operating region can be formed in a compact size.

According to the ninth aspect of the present invention, a gas is accommodated in the deforming section that has a deforming wall face, and an introduced liquid is accumulated in the non-deforming section that does not have a deforming wall face. Therefore, the introduced liquid is not influenced by the deformation of the deforming wall face, and it is possible to prevent the liquid from being attached and left on the deforming wall face. As a result, highly reliable quantitative processing can be performed.

According to the tenth aspect of the present invention, by pre-providing as a unit a plurality of the bellows type dispensing tips arranged in the tip arrangement holding section, on the dispensing head or the container set, and allowing it to move, the bellows type dispensing tips can be quickly replaced, and the efficiency of the processing can be improved.

According to the eleventh and twenty-second aspects of the present invention, a plurality of the bellows type dispensing tips are attached to the dispensing head as units of the tip arrangement holding section to thereby handle the bellows type dispensing tips. Therefore it is possible to collectively handle a large number of the bellows type dispensing tips easily.

According to the twelfth aspect of the present invention, a plurality of through holes are provided in the plate that serves as the tip arrangement holding section, and the bellows type dispensing tips are inserted into and held in the through holes. Therefore, the bellows type dispensing tips can be easily arranged.

According to the thirteenth aspect of the present invention, the state of the interior of the bellows type dispensing tip is detected to ascertain the presence and level of the liquid to determine whether or not suctioning/discharging is being precisely performed as instructed. As a result, highly reliable processing can be performed.

According to the fourteenth aspect of the present invention, the respective bellows type dispensing tips are loosely inserted and held, and the deformation of each bellows type dispensing tip is thereby regulated in the predetermined deformation direction. As a result, a more precise control can be performed.

According to the fifteenth aspect of the present invention, it is possible to provide a magnet so as to be able to come into close proximity to and move away from each accommodating section of the bellows type dispensing tip at once. Therefore, with a simple structure, it is possible to apply magnetic fields to the respective bellows type dispensing tips at once.

According to the seventeenth aspect of the present invention, the opening section is provided on the thin tube section, and therefore it can be inserted into various types of containers to perform suctioning, transferring, and discharging of a liquid, while it is suitable for automation and is easy to handle. Moreover, by forming the thin tube section in a tapered or sharp shape and providing it with rigidity, then even in the case of handling a pre-packed type container that pre-accommodates and film-seals a liquid solution such as reagent therein, it is possible to directly pierce the film and suction the liquid solution such as a reagent inside the container, thereby preventing contamination and realizing a high level of reliability.

According to the eighteenth aspect of the present invention, the thin tube section is formed as a separate body from the transitional section, and is attached to the transitional section, thereby forming the bellows type dispensing tip. Consequently the thin tube section can be formed using a hard material rather than a soft material such as used for the deforming section. Therefore at the time of manufacture, it is possible to prevent a bend in the thin tube section due to the softness of the material and its shape being thinner than that of other portions. As a result, it is possible to provide bellows type dispensing tips with very small variation in their shape, thereby enabling highly reliable processing.

According to the nineteenth aspect of the present invention, by providing a holder through and in which the accommodating section is to be loosely inserted and held, then even if a deforming wall face is provided, the deforming wall face is externally held. Therefore when the deforming wall face is deformed, this can be guided so as to allow deformation of the deforming wall face in a predetermined constant pattern. As a result, processing can be performed with a high level of quantitative reliability.

According to the twentieth aspect of the present invention, the thin tube section is provided so as to project from the holder, and therefore processing can be performed while the accommodating section is being loosely inserted in the holder. Moreover, the thin tube section can be supported more firmly, and therefore shifting of positions caused by deformation of the deforming wall face can be suppressed, and processing can be performed with an even higher level of reliability.

BEST MODE FOR CARRYING OUT THE INVENTION

Next, a bellows type dispensing tip and a bellows type dispensing apparatus that uses the bellows type dispensing tip according to embodiments of the present invention are described, with reference to the drawings.

FIG. 1 (a) conceptually shows a bellows type dispensing tip 11 according to a first embodiment of the present invention being supported on a dispensing head 70 of a bellows type dispensing apparatus 10 described later. In the bellows type dispensing tip 11, there are provided: a substantially cylindrical shaped longitudinal accommodating section (14, 15) having an axis thereof along the vertical direction, that is capable of accommodating a liquid or gas within the interior thereof surrounded by a substantially cylindrical shaped wall face, and that has a bellows 12 serving as a deformable deforming wall face in a portion of the wall face; and an opening section 13 provided so as to surround the axis thereof at the bottom end of the accommodating section, that communicates with the accommodating section (14, 15) and that enables inflow and outflow therethrough of a liquid suctioned or discharged by deformation of the bellows 12.

The bellows 12 is deformably provided in a portion of the wall face of the accommodating section (14, 15) so as to separate the wall face into an upper portion and lower portion, and with the vertical direction as the deformation direction. Respective peaks (nine peaks in this example) and valleys (eight valleys in this example) of the waveform or folds of the bellows 12 are formed perpendicular to the above vertical direction, and each of the valleys and peaks forms a circumference in each of their horizontal planes. The accommodating section (14, 15) has a deforming section 14 having the bellows 12 and capable of accommodating a gas, and a non-deforming section 15 that communicates with the deforming section 14, that does not have the bellows 12 as the deforming wall face, that has the opening section 13 on the tip end thereof, and that is capable of accumulating a liquid therein.

A top end face 12a on the top end of the deforming section 14 is provided so as to be able to come in contact with a presser plate 20 that corresponds to a movable member of the dispensing head 70 of the bellows type dispensing apparatus 10 described later, on which the bellows type dispensing tip 11 is supported, and it is moved vertically by the vertical movement of the presser plate 20 so that the bellows 12 expands and contracts in the vertical direction. Moreover, on the bottom end of a lower section 12b of the deforming section 14, there is provided a step portion. By means of this step portion the bellows type dispensing tip 11 is supported by the horizontal supporting plate 19 of the dispensing head 70. The non-deforming section 15 of the bellows type dispensing tip 11 passes through a hole provided in the horizontal supporting plate 19 so as to project downward from the horizontal supporting plate 19.

The non-deforming section 15 has: a substantially cylindrical shaped thick tube section 16 that communicates with the deforming section 14 and that connects to the lower section 12b on the upper side thereof; a substantially cylindrical shaped thin tube section 18 having the opening section 13 on the bottom end thereof; and a funnel shaped transitional section 17 that connects between the thick tube section 16 and the thin tube section 18.

FIG. 1 (a) shows a state with the presser plate 20 separated from the top end face 12a, which is a natural state with no deformation applied. That is to say, FIG. 1 (a) indicates that when the presser plate 20 is removed from the bellows type dispensing tip 11, the bellows 12 itself is biased so that the bellows 12 expands until it has attained this state.

FIG. 1 (b) to FIG. 1 (d) show the states in order, where presser plate 20 is further lowered while the presser plate 20 is contacted with the top end face 12a. For example, FIG. 1 (c) shows a position of the presser plate 20 serving as a movable member in a state of being able to both expand and contract the interior thereof due to the deformation of the bellows 12. This position is, for example, taken as a predetermined reference position, and control is performed with this state as a reference. Accordingly, FIG. 1 (b) shows a state where the bellows are expanded beyond the reference position. In the control, this state (a state where the bellows 12 is slightly contracted) shows a state where the liquid is suctioned at the maximum level, that is, a predetermined maximum suction state.

Moreover, FIG. 1 (d) is a state where the presser plate 20 has been lowered most, that is, a state where further contraction is no longer possible. In this state, the bellows type dispensing tip 11 has discharged all of the liquid that has been suctioned in the state of FIG. 1 (b). The reference position may be decided so that a state with a maximum suction of the liquid is a state where the bellow 12 is expanded to the position where the presser plate 20 is fully separated from the top end face 12a.

FIG. 2 shows an example of a cartridge container 21 according to a second embodiment suitable for the bellows type dispensing tip 11. FIG. 2 (a) is a side view showing a state where the thin tube section 18 of the bellows type dispensing tip 11 is inserted into a liquid accommodating section 22 of the cartridge container 21, and FIG. 2 (b) is an exploded perspective view of the cartridge container 21.

The cartridge container 21 is such that the top end of each of four of the liquid accommodating sections 22 is attached to a region around each of four holes 28 provided in an upper plate 23, and each liquid accommodating section 22 projects downward from the lower side of the upper plate 23. The upper plate 23 is horizontally mounted on the upper side of a channel shaped container supporting frame 24, and two transparent gauging side plates 25 are fitted on both sides of the container supporting frame 24. In positions on the gauging side plate 25 corresponding to the respective liquid accommodating sections 22, there are provided scale marks 26 that indicate liquid levels. Furthermore, in a corner of each gauging side plate 25, there may be provided a gauge identification number 27 for identifying the gauging side plate 25. In a position above the gauge identification number 27 there may be provided a region 27a for placing a bar code indicating the gauge identification number 27 or for placing a color code.

Next, a bellows type dispensing apparatus 10 according to a third embodiment is described, with reference to FIG. 3 to FIG. 6.

FIG. 3 is a front view of the bellows type dispensing apparatus 10 according to the present embodiment. The bellows type dispensing apparatus 10 is such that on a stage 30, there are provided: a dispensing head 70 that supports six of the bellows type dispensing tips 11 for suctioning or discharging a liquid into or from each bellows type dispensing tip 11 by deforming the bellows 12 of the bellows type dispensing tip 11; a container set 31 having a plurality (six in this example) of reagent accommodating containers 32 capable of accommodating various kinds of liquids, reagents, specimens and the like; and a head moving section (44, 45, 46) for moving the dispensing head 70 with respect to the container set 31. Reference symbol 30a denotes a supporting member that supports the stage 30.

The dispensing head 70 serving as a tip supporting section that supports a series of six of the bellows type dispensing tips 11, has the horizontal supporting plate 19 having six supporting holes for supporting the bellows type dispensing tips 11, and a vertical supporting plate 19a. The horizontal supporting plate 19 and the vertical supporting plate 19a are formed by bending a single plate at right angles, and respective right angled triangle shaped members 19b (FIG. 4) are attached so as to cover opposite side ends of the space between the horizontal supporting plate 19 and the vertical supporting plate 19a, thereby increasing the rigidity of the structure. To opposite end side portions of the horizontal supporting plate 19, there are attached the bottom end sections of two guide shafts 37, and the top end of each guide shaft 37 is attached to a tip securing upper plate 38 of the dispensing head 70. On each guide shaft 37 there are fitted tube shaped members 36 so as to be able to move vertically along the guide shaft 37. The tube shaped members 36 are connected to opposite ends of the presser plate 20 so as to maintain the presser plate 20 horizontal.

The presser plate 20 is respectively in contact with the top end face 12a of each of the six bellows type dispensing tips 11, and on the upper side of the presser plate 20 there is provided a rod shaped member 42 that projects upward. The rod shaped member 42 is provided so as to pass completely through a through hole 43 provided in the tip securing upper plate 38 to reach the upper side. The top end of the rod shaped member 42 is slidably in contact with a disk cam 41 eccentrically attached to a rotating disk 40. Rotation of the rotating disk 40 causes the rod shaped member 42 in contact with the disk cam 41 to move in the vertical direction, and consequently the presser plate 20 moves in the vertical direction, deforming the bellows 12. Reference symbol 39 denotes a motor for rotating the rotating disk 40. In this manner, in the present embodiment, movement of the presser plate 20 in the vertical direction is performed by this cam mechanism (39, 40, 41, 42).

The dispensing head 70 has a horizontal protuberance 33a on the lower side of both of side plates of a frame body 33. The protuberance 33a is movably engaged with two rail members 46b attached on the stage 30 while being sandwiched by a number of ball bearings arranged in two straight lines. The frame body 33 is attached to a belt 46 by an arm member 46a. The belt 46 is provided such that a roller 45 rotation-driven by a motor 44 provided on the stage 30 enables the belt 46 to travel along the direction of the rail members 46b. The horizontal supporting plate 19, the vertical supporting plate 19a, the tip securing upper plate 38, and therefore the bellows type dispensing tip 11 are attached so as to be able to move vertically with respect to the frame body 33.

FIG. 4 is a side view of the bellows type dispensing apparatus 10. This bellows type dispensing apparatus 10 has: a pinching tool 57 that, on the upper side of the horizontal supporting plate 19 that secures the bellows type dispensing tip 11, pinches one peak at the bottom end of the bellows 12 of the bellows type dispensing tip 11 from above and below the peak so as to support the bellows type dispensing tip 11; and a pinching tool attachment rod 58 that attaches the pinching tool 57 to the tip securing upper plate 38 and that is capable of adjusting the pinching position thereof. Accordingly, for the both-way deformation of the bellows type dispensing tip 11 in the case of performing a downward deformation to contract it and also in the case of expanding it upward, the position and the shape of the opening section 13 are not changed by the deformation of the bellows 12.

The vertical supporting plate 19a is attached to a vertical movement supporting plate 50, and to the vertical movement supporting plate 50, there are rotatably attached four guiding rollers 51, 52. On the upper side of an upper plate 49 of the frame body 33, there is provided a motor 47 for vertically moving the vertical movement supporting plate 50. There are further provided a roller 48 rotation-driven by the motor 47 and a roller 54 provided on a lower plate 34, and a belt 56 spans between the roller 48 and the roller 54. The vertical movement supporting plate 50 is attached to the belt 56, and moves vertically according to the traveling movement of the belt 56.

The container set 31 has: the reagent accommodating containers 32 accommodating reagents therein; a series of ten wells 60 capable of accommodating various kinds of liquid solutions; and a series of two tip accommodating sections 61 capable of accommodating the bellows type dispensing tips 11, and it is provided so as to be fixed on the stage 30.

Permanent magnets 35 are provided as magnetic devices so as to be able to move toward and away from the bellows type dispensing tip 11. On the lower side of bearers that support the permanent magnets 35, there are provided two rollers 63, so that the permanent magnets 35 are fitted into channels along the left-right direction provided on the lower plate 34 and can smoothly move in the left-right direction. The permanent magnets 35 are driven by a stepping motor, the motor shaft of which can move in the left-right direction in the drawing.

FIG. 5 is a plan view of the bellows type dispensing apparatus 10. The dispensing head 70 is capable of moving on the stage 30 in the left-right direction along the rail members 46b above the container set 31.

FIG. 6 is a rear view of the bellows type dispensing apparatus 10. In the center of the vertical movement supporting plate 50 there is provided a belt attachment fixture 62 for attaching the vertical movement supporting plate 50 onto the belt 56. Moreover, on both sides of the vertical movement supporting plate 50 there are rotatably provided the respective guiding rollers 51 and 52 engaged with guiding rails 53 so as to guide the vertical movement of the vertical movement supporting plate 50.

Next, FIG. 7 shows a bellows type dispensing apparatus 100 according to a fourth embodiment. Reference symbols the same as those for describing the above bellows type dispensing apparatus 10, denote the same components, and descriptions thereof are omitted.

The dispensing head 170 of the bellows type dispensing apparatus 100 employs a link mechanism (64, 65, 66, 67, 68) instead of the cam mechanism (39, 40, 41, 42) employed as a mechanism for performing deformation of the bellows type dispensing tip 11 according to the third embodiment.

The bellows type dispensing apparatus 100 according to the fourth embodiment is such that the presser plate 20 is in contact respectively with the top end face 12a of each of the six bellows type dispensing tips 11, and there are provided: a rod member 64 that projects upward on the upper side of the presser plate 20; a crossbar pivot 65 provided on the top end of the rod member 64; two link rods 66 that have one end rotatably connected to the pivot 65 and that are supported at supporting points 66a provided on supporting rods 66b; translation shafts 68 capable of moving in the vertical direction with their tip ends rotatably connected to the other end of the link rod 66; and stepping motors 67 for moving the translation shafts 68 in the vertical direction. Thus, the presser plate 20 is moved in the vertical direction.

FIG. 8 shows holders 71 and 72 according to fifth and sixth embodiments, into which the bellows type dispensing tips 11 can be loosely inserted.

The holder 71 according to the fifth embodiment shown in FIG. 8 (a) has an upper side opening section 73 provided on the upper side thereof, and a lower side opening section 74 for externally exposing the opening section 13. The bellows type dispensing tip 11 is inserted through the upper side opening section 73 so as to be loosely inserted into the interior of the holder 71. The holder 71 comprises a thick frame section 75 and a thin frame section 76 provided on the lower side thereof, and the lower side opening section 74 is provided on the tip end of the thin frame section 76. The thin frame section 76 engages with and supports the thin tube section 18 of the bellows type dispensing tip 11 so as to prevent wobbles of the thin tube section 18. In this case, deformation is performed by an insertion tool 77 that is attached to the presser plate 20 and can come into contact with the top end face of the bellows type dispensing tip 11 through the upper side opening section 73 of the holder 71.

The holder 72 according to the sixth embodiment shown in FIG. 8 (b) has an upper side opening section 78 provided on the upper side thereof, and a lower side opening section 79 for externally exposing the opening section 13 of the bellows type dispensing tip 11. The bellows type dispensing tip 11 is inserted through the upper side opening section 78 so as to be loosely inserted into the interior of the holder 72. The holder 72 comprises a thick frame section 83 having a slit 80 provided in the side face thereof, and a thin frame section 81 provided on the lower side thereof, and the lower side opening section 79 is provided on the tip end of the thin frame section 81. The thin frame section 81 engages with and supports the thin tube section 18 of the bellows type dispensing tip 11 so as to prevent wobbles of the thin tube section 18. In this case, deformation is performed by an insertion tool 82 that is attached to the presser plate 20 and can come into contact with the top end face of the bellows type dispensing tip 11 through the slit 80 provided in the side face of the thick frame section 83.

With use of these holders 71 and 72, it is possible to prevent movement of the opening section 13, while preventing unwanted deformation in the shape of the bellows type dispensing tip 11, and securing the bellows type dispensing tip 11. Moreover, since the deformation of the bellows type dispensing tip 11 is guided along the axial direction by the holders 71 and 72, it is possible to have smooth deformation, to have regularity in the deformation of the bellows type dispensing tip 11, and to obtain an accurate internal capacity according to the degree of deformation to be performed.

Next, a bellows type dispensing tip 111 according to a seventh embodiment is described based on FIG. 9. FIG. 9 (a) is an enlarged sectional view of the bellows type dispensing tip 111, and FIG. 9 (b) is a perspective view thereof. The bellows type dispensing tip 111 is such that there are provided: a substantially cylindrical shaped longitudinal accommodating section (114, 115) having an axis thereof along the vertical direction, that is capable of accommodating a liquid or gas within the interior thereof surrounded by a substantially cylindrical shaped wall face, and that has a bellows 112 serving as a deformable deforming wall face in a portion of the wall face; and an opening section 113 surrounding the axis thereof at the bottom end of the accommodating section, that communicates with the accommodating section (114, 115) and that enables inflow and outflow therethrough of a liquid suctioned or discharged by deformation of the bellows 112.

The bellows 112 is provided in a portion of the wall face of the accommodating section (114, 115) so as to separate the wall face into an upper portion and lower portion, while being capable of deforming itself in the vertical deformation direction. Respective peaks (four peaks in this example) and valleys (five valleys in this example) of the waveform or folds of the bellows 112 are formed perpendicular to the above vertical direction, and each of the valleys and peaks forms a circumference in each of their horizontal planes. The accommodating section (114, 115) has a deforming section 114 having the bellows 112 and capable of accommodating a gas, and a non-deforming section 115 that communicates with the deforming section 114, that does not have the bellows 112 as the deforming wall face, that has the opening section 113 on the tip end thereof, and that is capable of accumulating a liquid therein.

A top end face 112a on the top end of the deforming section 114 is provided so as to be able to come in contact with a presser plate 120 that corresponds to a movable member of a dispensing head 270 of a bellows type dispensing apparatus 110 described later, on which the bellows type dispensing tip 111 is supported, and it is moved vertically by the vertical movement of the presser plate 120 so that the bellows 112 expands and contracts in the vertical direction. A lower section 112b of the deforming section 114 does not deform by expansion or contraction of the bellows 112.

The non-deforming section 115 has: a substantially cylindrical shaped thick tube section 116 that communicates with the deforming section 114 and that connects to the lower section 112b on the upper side thereof; a substantially cylindrical shaped thin tube section 118 having the opening section 113 on the bottom end thereof; and a funnel shaped transitional section 117 that connects between the thick tube section 116 and the thin tube section 118.

The transitional section 117, on the upper side thereof, has a fitting section 117c to be inserted and fitted into and held in each of substantially tapered through holes 123 provided in a plate of a rack 121 serving as a tip arrangement holding section described later, and on the lower side of the transitional section 117, there is provided an interior detection region 117a sandwiched by parallel transparent flat plate side faces. Furthermore, at the bottom end section of the transitional section 117, there is provided a socket shaped section 117b into which the top end section of the separately provided thin tube section 118 is fitted and attached with use of an adhesive or by means of thermal welding or ultrasonic welding.

The transitional section 117 includes a complex shape such as that of the interior detection region 117a. However the deforming section 114, the thick tube section 116 and the transitional section 117 may be integrally formed by means of blow molding. Moreover, the thin tube section 118 may be rigidly formed by means of injection molding, and connected to the transitional section at the socket shaped section 117b. Since there is provided the interior detection region 117a, it is possible to detect the state inside the thin tube section by measuring the light passing therethrough as a result of irradiating a light beam in a direction normal to the transparent flat plate side faces.

FIG. 10 is a side sectional view showing a state of a rack 121 according to an eighth embodiment serving as the tip arrangement holding section having the bellows type dispensing tips 111 arranged therein in a grid having 12 columns and 8 rows at predetermined intervals, being detachably mounted on a rack supporting base 126 provided on the aforementioned container set. The rack 121 has a plate 122 in which the through holes 123 are arranged in a grid having 12 columns and 8 rows. Each of the through holes 123 is provided in a tapered shape so as to fit with the fitting section 117c of the transitional section 117 of the bellows type dispensing tip 111. In a state of being held in each of the through holes 123, the thin tube section 118 of each of the bellows type dispensing tips 111 and the interior detection region 117 are positioned below the plate 122, and the bellows 112 is positioned above the plate 122. The interior of the rack supporting base 126 is partitioned into a plurality of chambers in columns and rows by partitioning walls 126a so that the thin tube sections 118 do not come into contact with each other.

Moreover, in four corners around each of the bellows type dispensing tips 111, there are respectively provided four rods 125, the height of which corresponds to the bellows type dispensing tip 111 in a non-deformed state, in the upward direction from the upper side of the top face of the plate 122, allowing loose insertion of each bellows type dispensing tip 111. These four rods 125 correspond to the loose insertion section in the claims. Thus, the deformation direction of the bellows type dispensing tip 111 is controlled so as to be maintained in the vertical direction, thereby maintaining its constant deforming pattern. On the upper side and lower side of the plate 122, there are provided attachment grooves 124 along both edge sections of the plate 122 for attaching a dispensing head 270 described later.

FIG. 11 (a) is a plan view of the rack 121. The through holes 123 are arranged at predetermined intervals in a grid having 12 columns and 8 rows. FIG. 11 (b) is a plan view of a rack 221. Through holes 223 are arranged in a grid having 24 columns and 16 rows at intervals narrower than those of the rack 121. In the respective through holes 223, there are respectively provided four rods 225 serving as the loose insertion section.

FIG. 12 shows the bellows type dispensing apparatus 110 according to the eighth embodiment in a state with the bellows type dispensing tips 111 attached.

The bellows type dispensing apparatus 110 is provided with: a dispensing head 270 that supports the bellows type dispensing tips 111 in a grid having 12 columns and 8 rows, by attaching the rack 121 thereon, and that performs suction and discharge of a liquid into and from the bellows type dispensing tips 111 when the bellows 112 are deformed; a container set 131 having a plurality of reagent accommodating containers 132 capable of accommodating various kinds of liquids, reagents, and specimens; and a head shifting section (not shown in the drawing) that moves the dispensing head 270 with respect to the container set 131.

The dispensing head 270 is provided with two attachment supporting members 119 that respectively fit and attach the rack 121 having the through holes 123 in 12 columns and 6 rows and holding the bellows type dispensing tips 111, to attachment grooves provided on both edge sections of the rack 121. These two attachment supporting members 119 correspond to the tip supporting sections. These two attachment supporting members 119 are provided along the lower edge section of a box shaped frame body 133. Therefore, the plate 122 of the rack 121 is provided so as to close off the opening section on the lower side of the frame body 133.

Within the frame body 133, there is provided a partitioning plate 138 that partitions the interior of the frame body 133 in the horizontal direction. The presser plate 120 that serves as a movable member for deforming the bellows 112 on the top end face 112a of each bellows type dispensing tip 111 is provided at the bottom end of a supporting plate 120a provided so as to pass through each gap 120b provided in the partitioning plate 138, and the supporting plate 120a is supported by a driving member 143. The driving member 143 is slidably guided, on both side portions thereof, by two guide shafts 137, and in the middle portion thereof, it is connected to a nut section screwed on a ball screw 141, thereby vertically moving in synchronization with the vertical movement of the nut section due to rotation of the ball screw 141. Reference symbol 139 denotes a motor that rotation-drives the ball screw 141, and reference symbol 140 denotes a shaft thereof.

Furthermore, as shown in FIG. 13, below the rack 121 of the dispensing head 270 there is provided a magnetic device 135 for exerting a magnetic force on the accommodating section 115 of the bellows type dispensing tip 111. The magnetic device 135 is provided so as to be able to relatively move in the row direction of the bellows type dispensing tips 111 arranged in a grid (with 12 columns and 8 rows in this example), and has: a total number (number of columns+1) of comb teeth members 135*a* that extend in the row direction and are provided at the above mentioned predetermined intervals of the rack 121, among which (number of columns−1; 11 in this example) of them excluding the two on both side ends are provided with widths that enable insertion between the above mentioned columns; and a supporting member 135*c* that is connected to one end of each of the comb teeth members 135*a*, so as to form an overall comb shape. On the comb teeth members 135*a* there are provided magnets as many as the number of rows (8 in this example) arranged at the predetermined intervals, in positions corresponding to the respective bellows type dispensing tips 111.

Furthermore, in the dispensing head 270, there is provided below the rack 121 and above the magnetic device 135 a light detection section 150 that transmits a light beam through the interior detection region 117*a* of each bellows type dispensing tip 111 for detecting the state of the interior. As shown in FIG. 13, the light detection section 150 is provided so as to be able to move relatively in the row direction of the bellows type dispensing tips 111 arranged in a grid (12 columns and 8 rows in this example), and has a total number (number of columns+1; 13 in this example) of comb teeth members 151 that extend in the row direction and are provided at the predetermined intervals, among which (number of columns−1; 11 in this example) of them excluding the two on both end sides are provided with widths that enable insertion between the columns, so as to form an overall comb shape. On the opposing faces of the comb teeth members 151 adjacent to each other in close proximity to the tip ends of the comb teeth members 151, there are respectively provided light emitting/light receiving section pairs 152 opposing each other so as to be on both sides of the interior detection region 117*a*. The light detection section 150 sequentially moves along the row direction to perform detection at once of the interiors of the bellows type dispensing tips 111 in twelve columns. At this time, the light detection section 150 may be able to move along a rail provided along the row direction on the plane face on the upper side of the magnetic device 135.

The respective embodiments described above are to give concrete descriptions of the present invention for better understanding, and are not to be considered as limiting other embodiments. Therefore, modifications may be made without departing from the scope of the invention. For example, deformation is performed mainly with the bellows in the above embodiments. However, the invention can also be realized with use of a deformation wall face in a shape other than a bellows shape, or with use of an elastic body such as rubber for the material of the deformation wall face, for example. Moreover, the shape of the bellows type dispensing tip is not limited to the shape described above, and it may have steps in the transitional section and may have steps in sections other than the transitional section.

Furthermore, the tip arrangement holding section is not limited to the arrangement described above, and a number such as 4, 6, 8, 12, 96, and 384 of the dispensing tips may be arranged in one column, in a grid, or in another shape.

Moreover, in the opening section of the thin tube section of the bellows type dispensing tip, there may be further fitted a small diameter short tube made of stainless steel or the like, to increase the level of dispensing precision.

INDUSTRIAL APPLICABILITY

A bellows type dispensing tip, a bellows type dispensing apparatus, and a method of bellows type dispensing processing according to the present invention relates to all kinds of fields in which various kinds of liquid solution processing are required, such as the industrial field, the agricultural field including food, agricultural production, seafood processing, the pharmaceutical field, the medical field involving hygiene, healthcare, immunity, pathology, and genetics, and the chemistry or biological science field. In particular, the present invention is effective when continuously executing a series of processes using a number of reagents and substances in a predetermined order.

Figure 1:
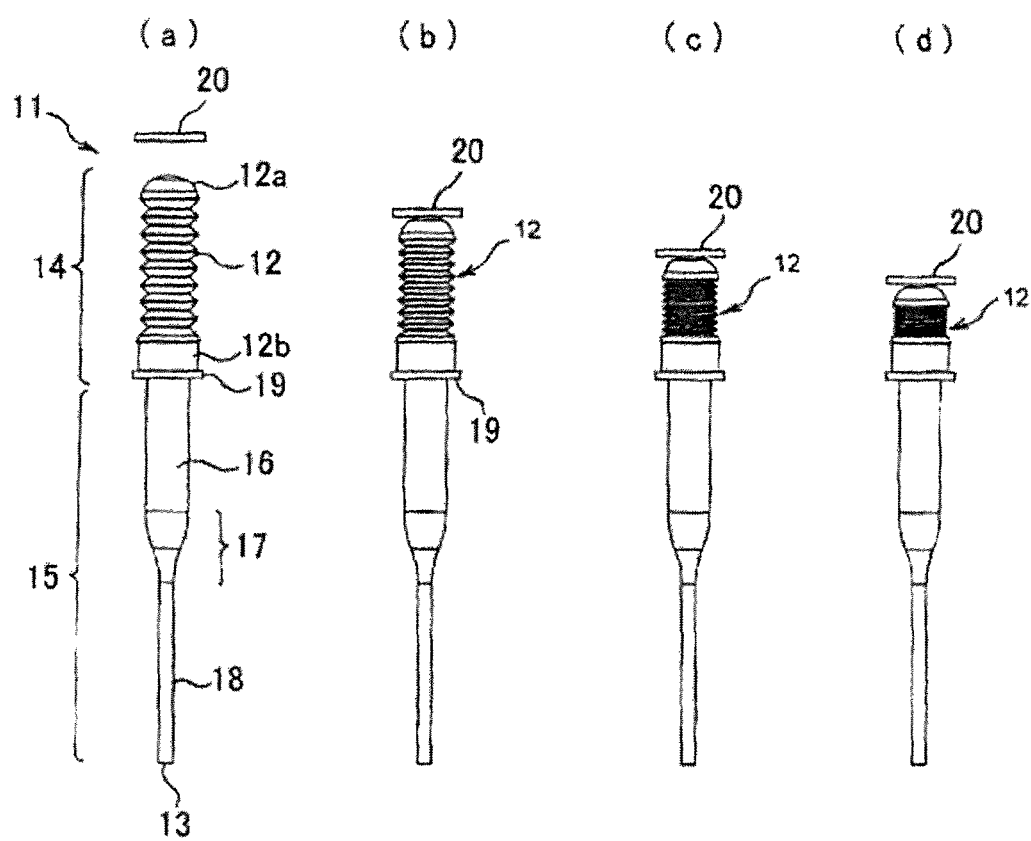
FIG. 1 is an explanatory drawing showing a bellows type dispensing tip and operation thereof according to a first embodiment of the present invention.
Figure 2:
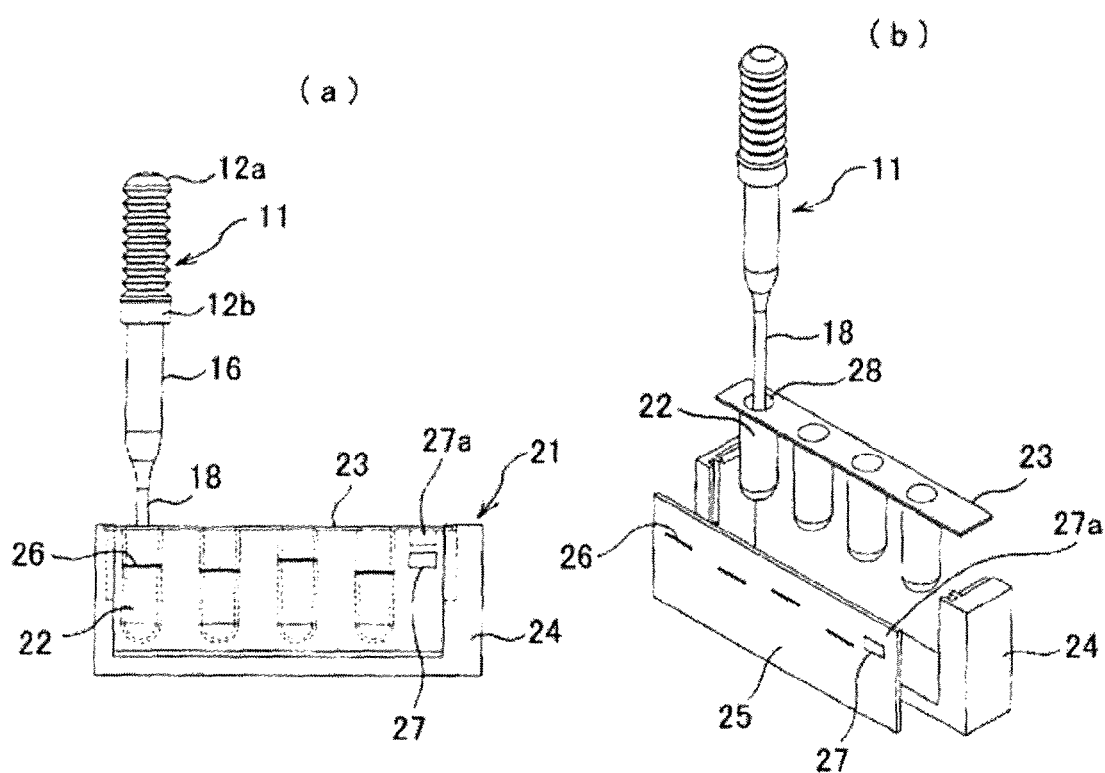
FIG. 2 is a drawing showing a suitable container for a bellows type dispensing tip according to a second embodiment of the present invention.
Figure 3:
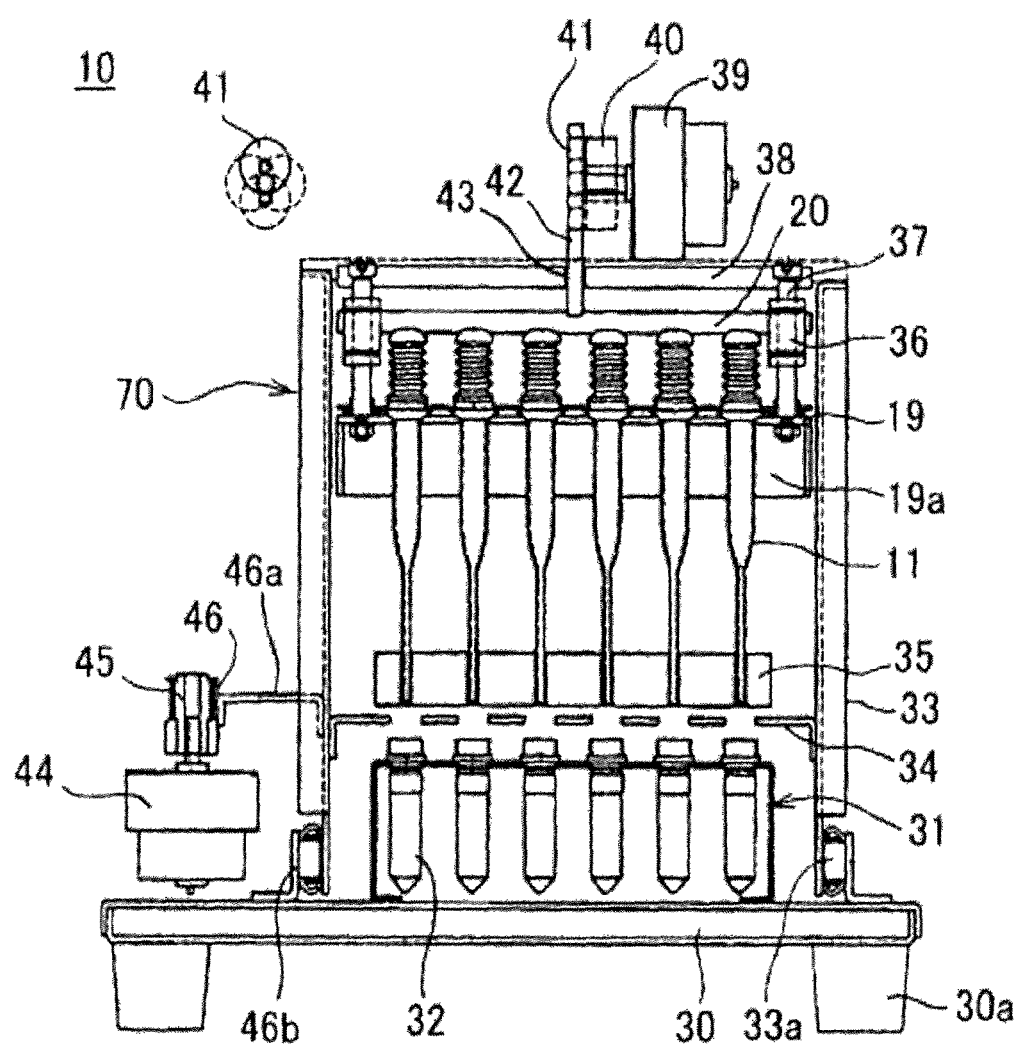
FIG. 3 is a front view of a bellows type dispensing apparatus according to a third embodiment of the present invention.
Figure 4:
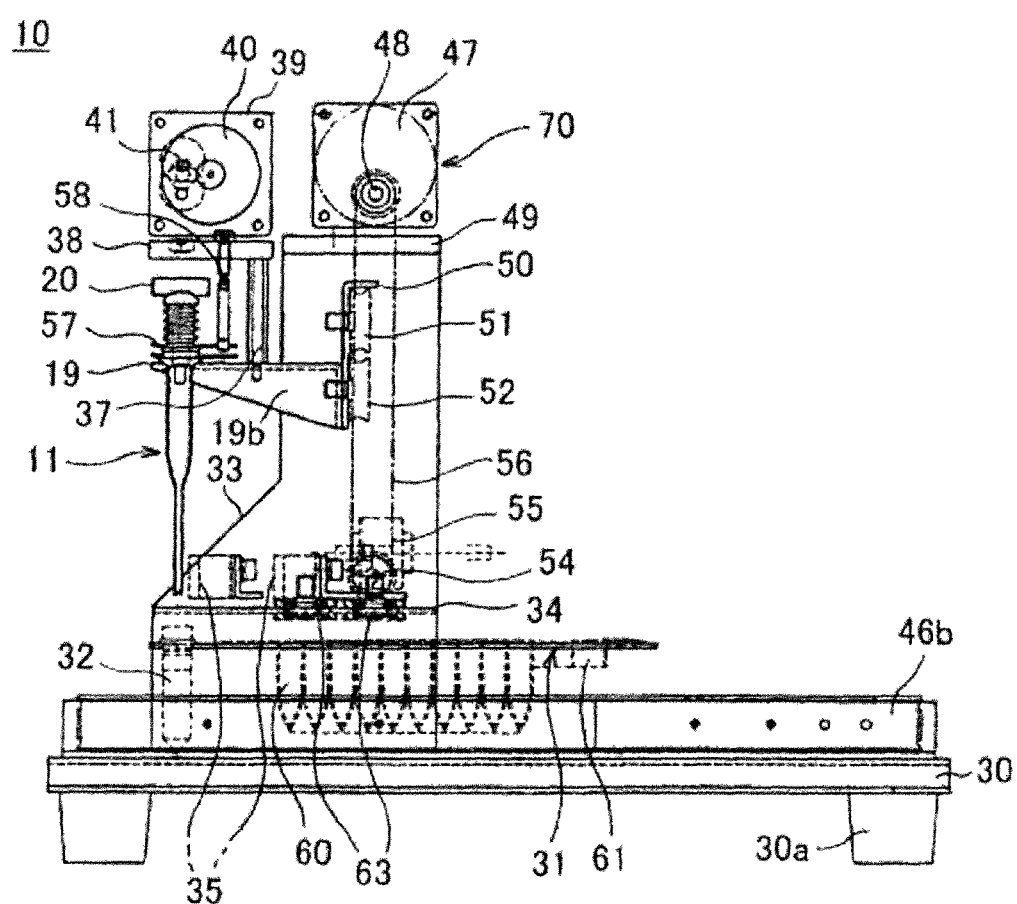
FIG. 4 is a side view of the bellows type dispensing apparatus according to the third embodiment of the present invention.
Figure 5:
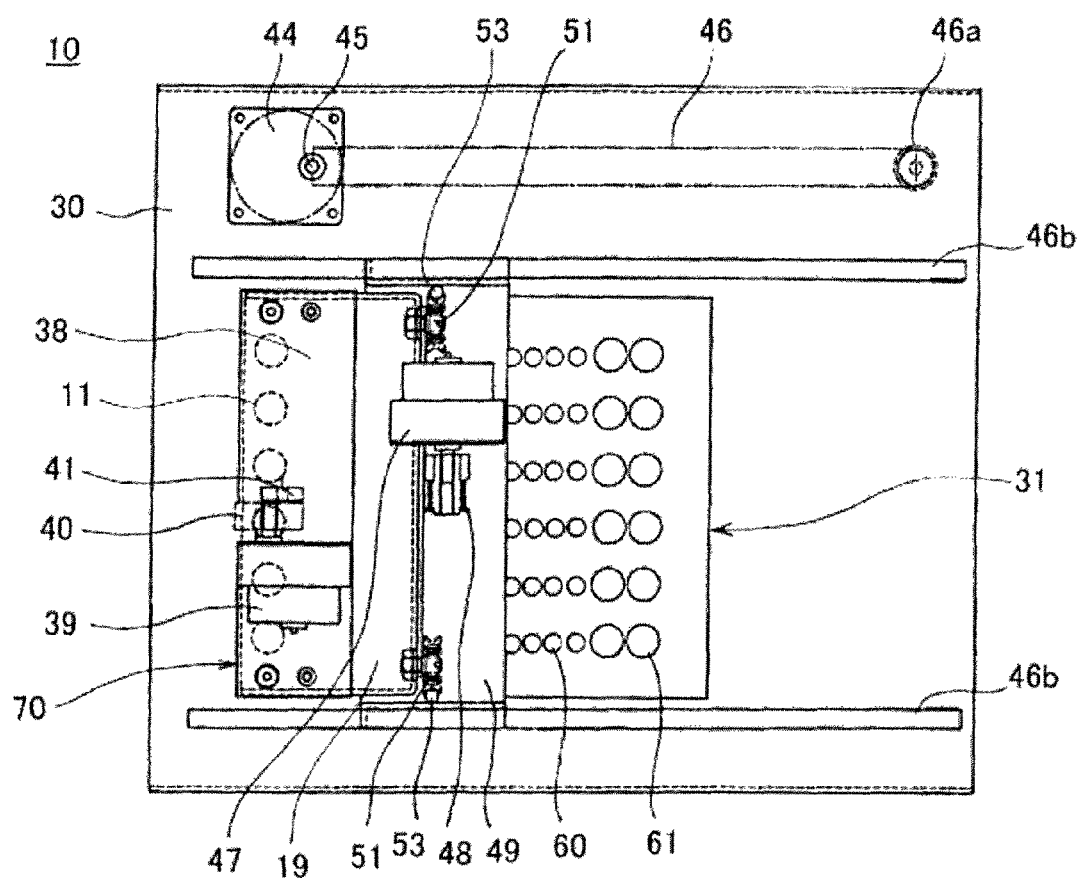
FIG. 5 is a plan view of the bellows type dispensing apparatus according to the third embodiment of the present invention.
Figure 6:
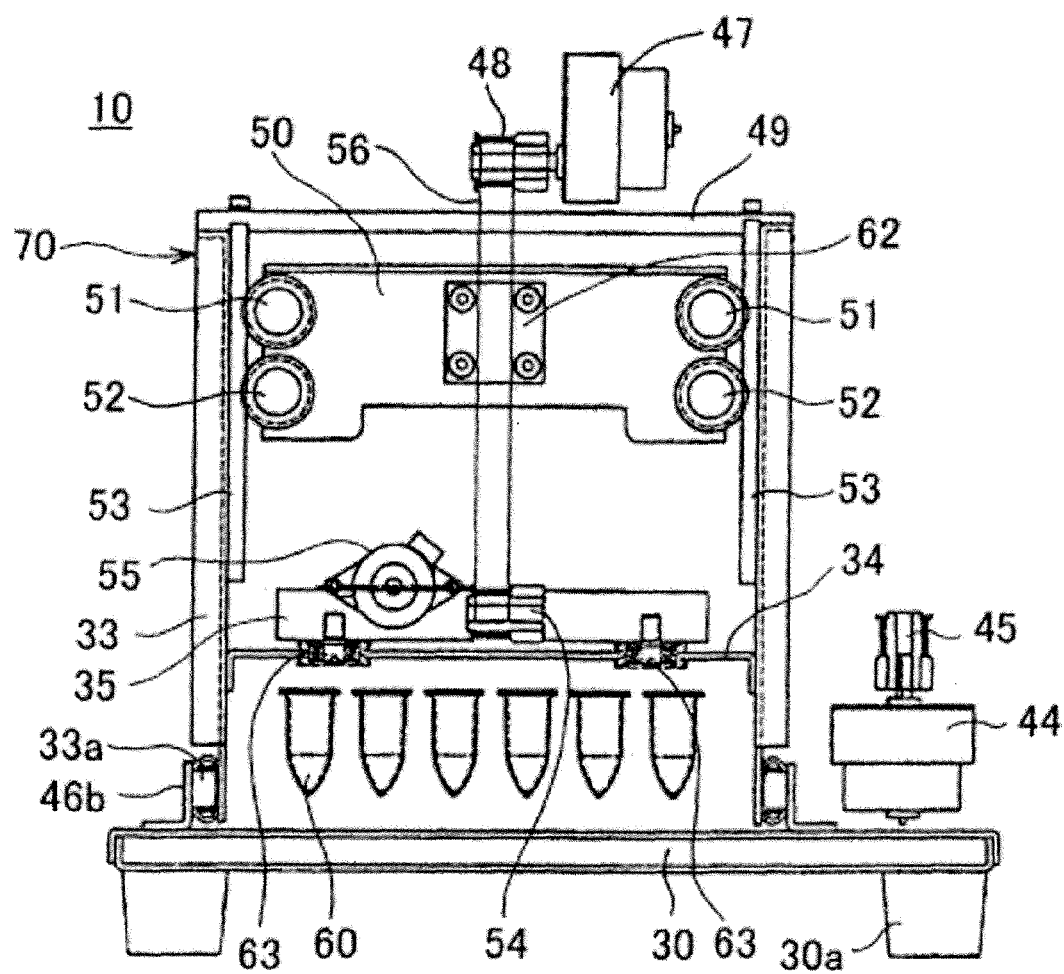
FIG. 6 is a rear view of the bellows type dispensing apparatus according to the third embodiment of the present invention.
Figure 7:
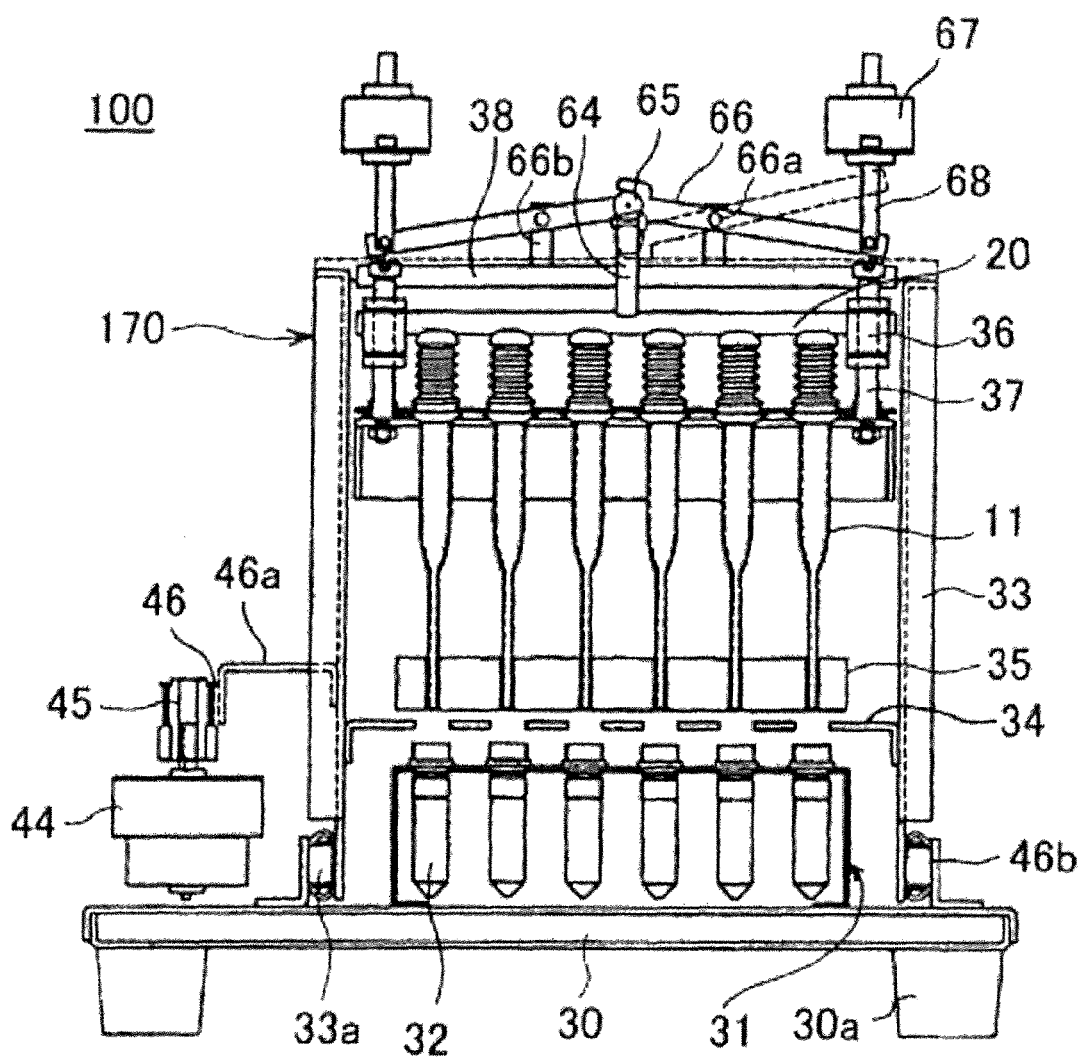
FIG. 7 is a front view of a bellows type dispensing apparatus according to a fourth embodiment of the present invention.
Figure 8:
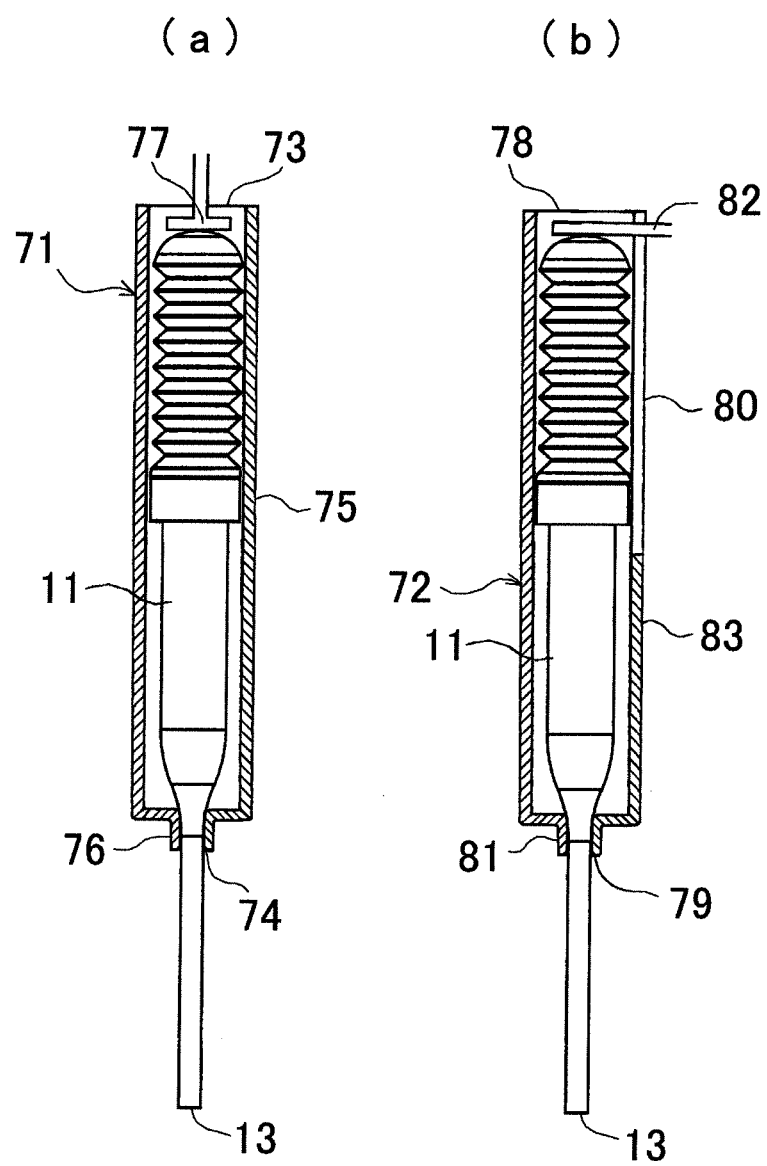
FIG. 8 is a drawing showing a holder according to fifth and sixth embodiments of the present invention.
Figure 9:
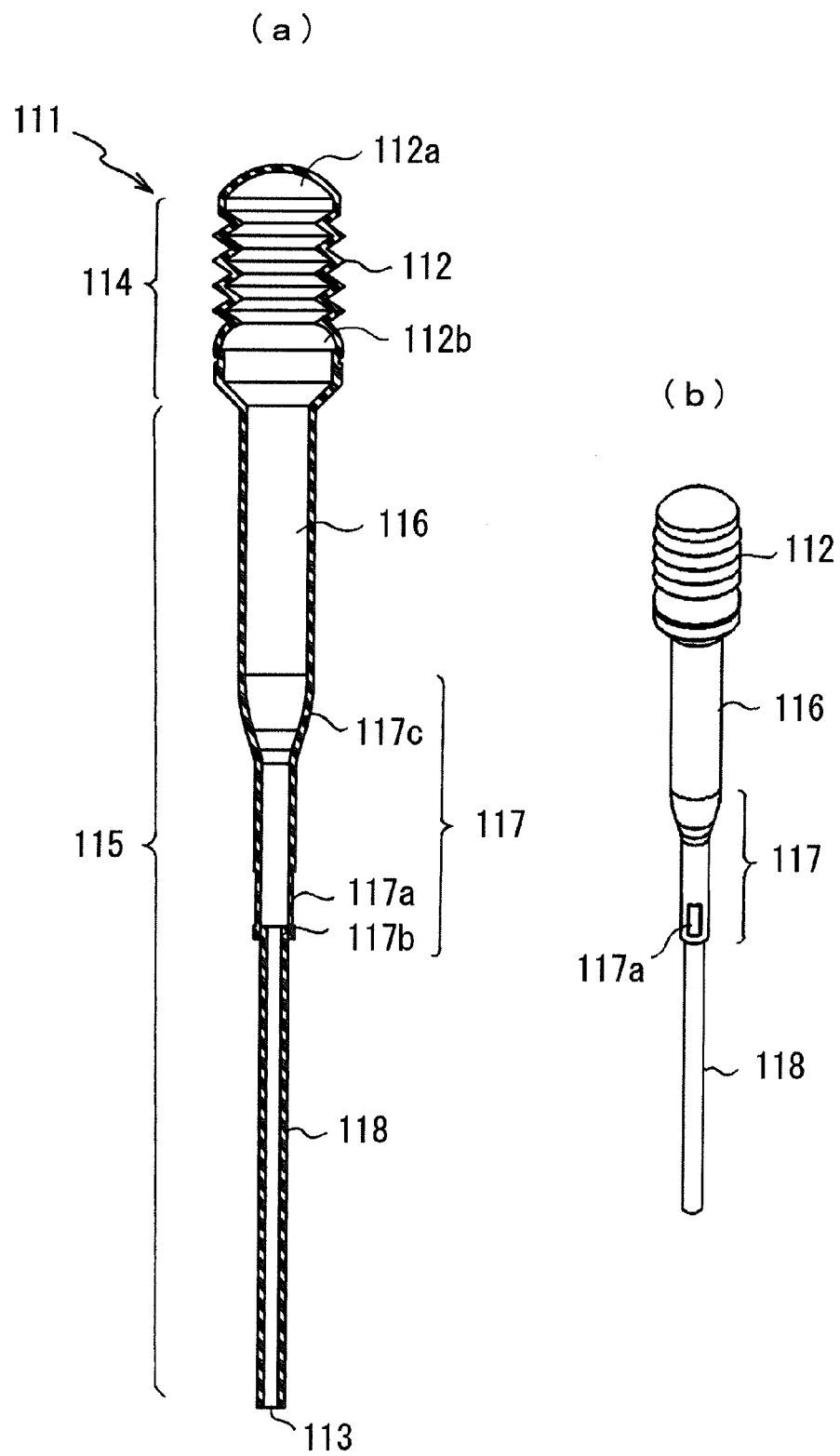
FIG. 9 is a drawing showing a bellows type dispensing tip according to a seventh embodiment of the present invention.
Figure 10:
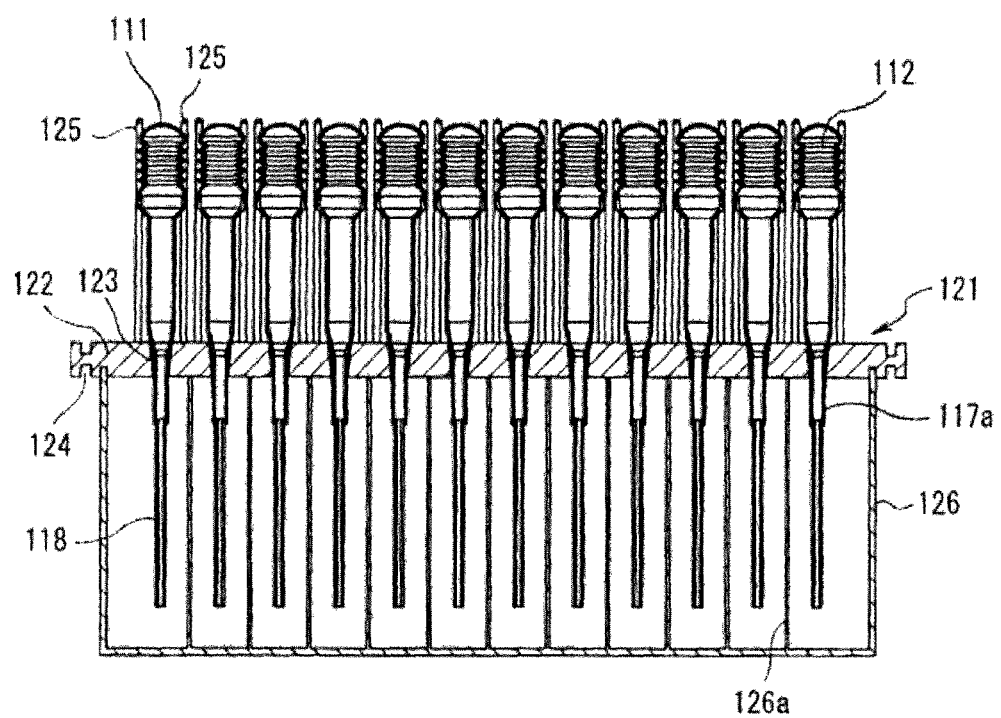
FIG. 10 is a sectional view showing a rack having bellows type dispensing tips arranged therein according to an eighth embodiment of the present invention.
Figure 11:
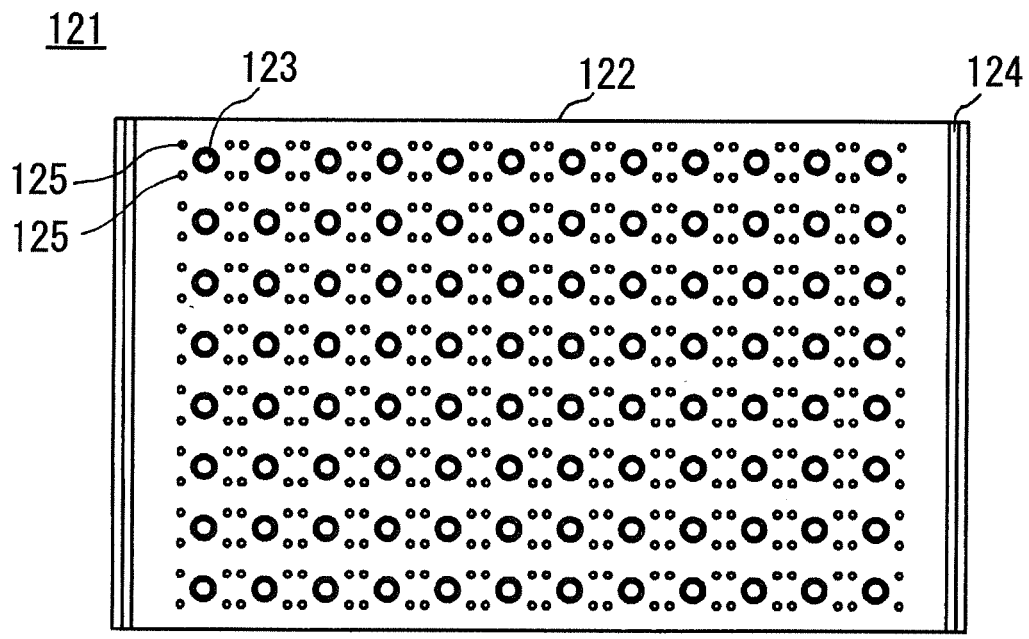
FIG. 11 is a plan view showing the rack according to the eighth embodiment of the present invention.
Figure 11:
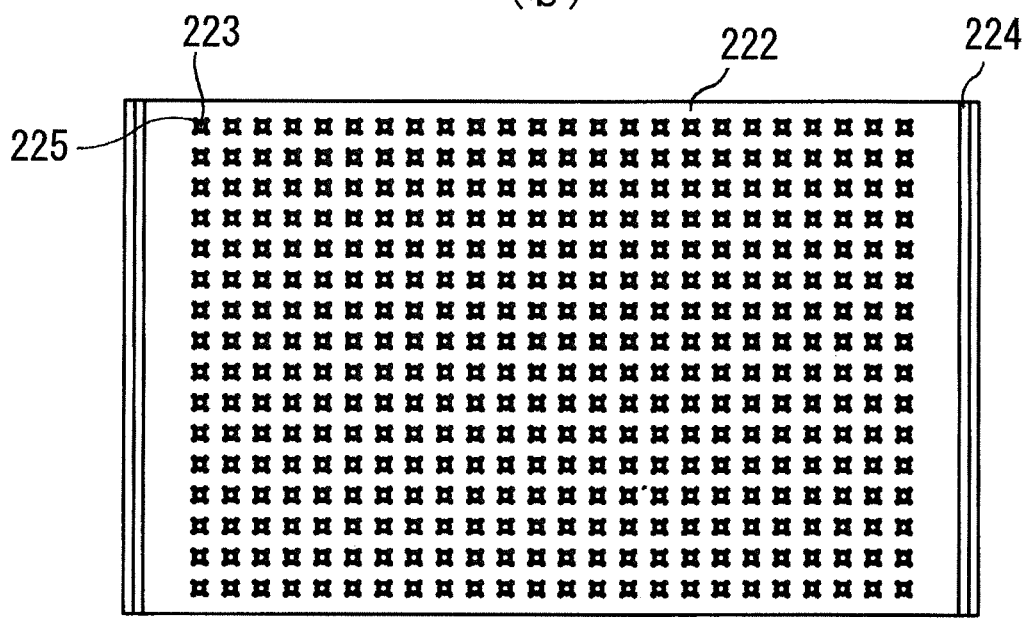
Figure 12:
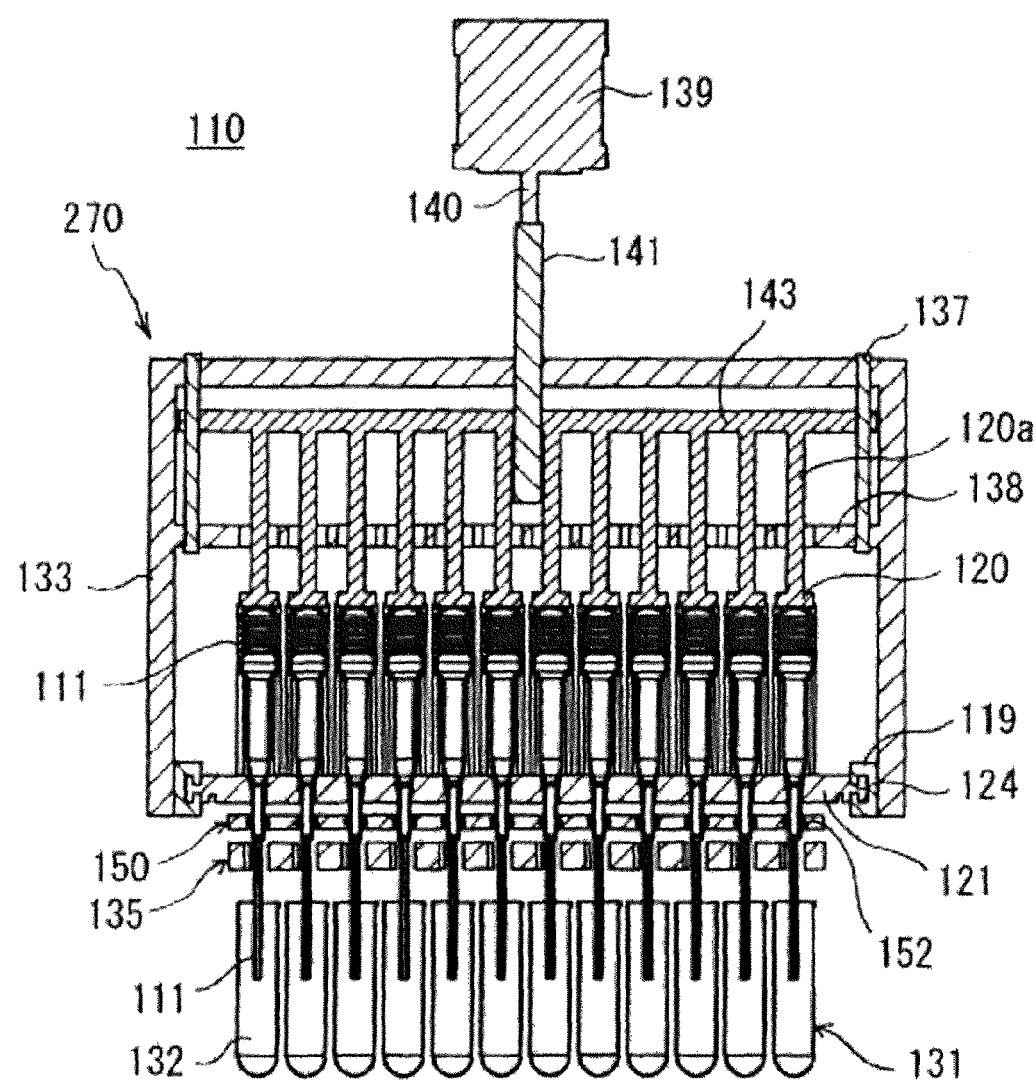
FIG. 12 is a sectional view showing a bellows type dispensing apparatus according to the eighth embodiment of the present invention.
Figure 13:
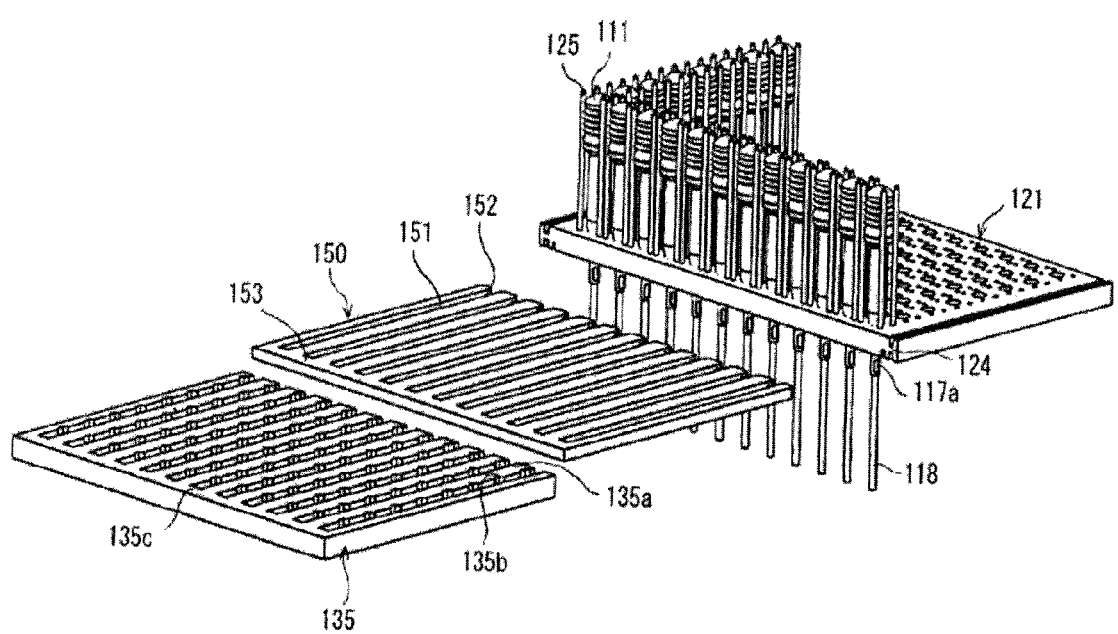
FIG. 13 is an exploded perspective view of the bellows type dispensing apparatus according to the eighth embodiment of the present invention.

The invention claimed is:

1. A bellows type dispensing tip comprising:
   an accommodating section that is capable of accommodating a liquid or gas in the interior thereof surrounded by a wall face and that has a deforming wall face in one portion of said wall face, capable of predetermined deformation without practically changing a total internal surface area of the wall face; and
   an opening section that is communicated with said accommodating section and that enables inflow and outflow of a liquid suctioned/discharged by expansion and contraction of said interior caused by deformation of said deforming wall face, and that can be inserted into a container capable of accommodating various kinds of liquid solutions;

wherein said opening section is provided at a bottom end of the bellows type dispensing tip; said deforming wall face is formed in one portion of the wall face surrounding said accommodating section so as to be able to deform in the vertical direction; and said accommodating section has; a deforming section capable of accommodating a gas, that is provided above said opening section, and that has said deforming wall face, and a non-deforming section capable of accommodating a liquid, that communicates with said deforming section, that does not have said deforming wall face, and that has said opening section on a tip end, wherein said deforming section comprises:
  an upper section that is deformable, the upper section comprising:
    the deforming wall face that is adapted to be deformed to contract or expand the interior, the deforming wall face having a top and a bottom, and
    a top end face adjacent the top of the deforming wall face,
    wherein the top end face is adapted to contact a movable member; and
  a lower section that is not deformable, the lower section being in communication with the upper section, the lower section having a top end and a bottom end,
    wherein the top end of the lower section is adjacent the bottom of the deforming wall face, and
    wherein a step portion is defined at the bottom end of the lower section, the step portion being adapted to contact a horizontal supporting plate at an opening formed through the horizontal supporting plate;

wherein said non-deforming section has:
  a thick tube section that communicates with said deforming section and that is connected to the step portion of the lower section;
  a thin tube section having said opening section; and
  a transitional section formed between said thick tube section and said thin tube section, wherein the non-deforming section is adapted to extend from the bottom end of the deforming section;

wherein the non-deforming section does not extend into the upper section that is deformable and thus the upper section and the non-deforming section are not radially overlapping;

wherein the lower section, which defines the step portion, is positioned between the non-deforming section and the upper section that is deformable so that the upper section is in communication with the non-deforming section via the lower section only; and wherein said thick tube section, said deforming section, and said transitional section are integrally formed, and a top end section of said thin tube section is fitted to a bottom end section of said transitional section, and attached by bonding or welding, and said thin tube section is formed from a member that is harder than said thick tube section, said deforming section, and said transitional section.

2. A bellows type dispensing tip according to claim 1, further having a holder for loose insertion and holding of said accommodating section, and said holder has an upper side opening section provided on an upper side thereof and a lower side opening section that enables said opening section to be externally exposed;

wherein the holder comprises:
  a thick frame section having a slit provided in a side face thereof, and
  a thin frame section provided on a lower side thereof, wherein the lower side opening section is provided on the tip end of the thin tube section, and the upper side opening section is provided on an upper side of the thick frame section.

3. A bellows type dispensing tip according to claim 1, wherein said non-deforming section is provided with an interior detection region interposed between transparent flat plate side faces parallel with each other.

4. A method of bellows type dispensing processing comprising:

a supporting step for supporting a plurality of bellows type dispensing tips having; an accommodating section that is capable of accommodating a liquid or gas in the interior thereof surrounded by a wall face, and that has a deforming wall face in a portion of said wall face, capable of a predetermined deformation without practically changing a total internal surface area of the wall face, and an opening section that is communicated with said accommodating section and that enables inflow and outflow of a liquid suctioned/discharged by expansion and contraction of said interior caused by deformation of the deforming wall face, on a dispensing head so that said opening section does not move due to deformation of said deforming wall face;

wherein the opening section can be inserted into a container capable of accommodating various kinds of liquid solutions;

wherein said opening section is provided at a bottom end of the bellows type dispensing tip; said deforming wall face is provided in a portion of a wall face surrounding said accommodating section so as to be able to deform in the vertical direction; said accommodating section has; a deforming section capable of accommodating a gas, that is provided above said opening section, and that has said deforming wall face, and a non-deforming section capable of accommodating a liquid, that communicates with said deforming section, that does not have said deforming wall face, and that has said opening section;

wherein said deforming section comprises:
  an upper section that is deformable, the upper section comprising:
    the deforming wall face that is adapted to be deformed to contract or expand the interior, the deforming wall face having a top and a bottom, and
    a top end face adjacent the top of the deforming wall face,
    wherein the top end face is adapted to contact a movable member; and
  a lower section that is not deformable, the lower section being in communication with the upper section, the lower section having a top end and a bottom end,
    wherein the top end of the lower section is adjacent the bottom of the deforming wall face, and
    wherein a step portion is defined at the bottom end of the lower section, the step portion being adapted to contact a horizontal supporting plate at an opening formed through the horizontal supporting plate;

wherein said non-deforming section has:
a thick tube section that communicates with said deforming section and that is connected to the step portion of the lower section;
a thin tube section having said opening section; and
a transitional section formed between said thick tube section and said thin tube section,
wherein the non-deforming section is adapted to extend from the bottom end of the deforming section;
wherein the non-deforming section does not extend into the upper section that is deformable and thus the upper section and the non-deforming section are not radially overlapping;
wherein the lower section, which defines the step portion, is positioned between the non-deforming section and the upper section that is deformable so that the upper section is in communication with the non-deforming section via the lower section only; and
wherein said thick tube section, said deforming section, and said transitional section are integrally formed, and a top end section of said thin tube section is fitted to a bottom end section of said transitional section, and attached by bonding or welding, and said thin tube section is formed from a member that is harder than said thick tube section, said deforming section, and said transitional section;
a moving step for moving said dispensing head; and
a deforming step for inserting said opening section into a container of a container set and deforming said deforming wall face at once,
wherein said deforming step sets a predetermined reference position for deformation of said deforming wall face, and deforms said deforming wall face, taking the reference position as a reference, and said predetermined reference position is determined based on at least one factor selected from; an amount of a liquid to be handled in processing, a capacity of the bellows type dispensing tip to be used, processing contents, and finishing precision of the bellows type dispensing tip.

5. A method of bellows type dispensing processing according to claim 4, wherein said supporting step is performed by attaching a tip arrangement holding section capable of detachably holding a plurality of said bellows type dispensing tips arranged in a line or in a plane face at predetermined intervals, to the dispensing head while allowing each of said bellows type dispensing tips to deform.

6. A method of bellows type dispensing processing according to claim 5 wherein said deforming step has a step for contacting or connecting a movable member with or to a top end face of said accommodating section, and a step for lowering and/or raising said movable member.

7. A method of bellows type dispensing processing according to claim 6, wherein raising and lowering of said movable member is performed by setting a predetermined reference position along the vertical direction in which said deforming wall face is deformed, and then using the reference position as a reference.

8. A method of bellows type dispensing processing according to claim 4, wherein in said liquid, a magnetic material that can bond with a predetermined substance or that has been bonded with a predetermined substance is suspended, and said magnetic material is attached to an inner wall of said accommodating section or said container and separated, by exerting a magnetic field on said accommodating section or a container of said container set.

9. A bellows type dispensing apparatus comprising:
one or two or more bellows type dispensing tips having;
an accommodating section that is capable of accommodating a liquid or gas in the interior thereof surrounded by a wall face, and that has a deforming wall face in a portion of said wall face, capable of predetermined deformation without practically changing a total internal surface area of the wall face, and an opening section that is communicated with said accommodating section and that enables inflow and outflow of a liquid suctioned/discharged by expansion and contraction of said interior caused by deformation of said deforming wall face;
wherein the opening section can be inserted into a container capable of accommodating various kinds of liquid solutions;
wherein said opening section is provided at a bottom end of the bellows type dispensing tip; said deforming wall face is provided in a portion of a wall face surrounding said accommodating section so as to be able to deform in the vertical direction; said accommodating section has; a deforming section capable of accommodating a gas, that is provided above said opening section, and that has said deforming wall face, and a non-deforming section capable of accommodating a liquid, that communicates with said deforming section, that does not have said deforming wall face, and that has said opening section;
wherein said deforming section comprises:
an upper section that is deformable, the upper section comprising:
the deforming wall face that is adapted to be deformed to contract or expand the interior, the deforming wall face having a top and a bottom, and
a top end face adjacent the top of the deforming wall face,
wherein the top end face is adapted to contact a movable member; and
a lower section that is not deformable, the lower section being in communication with the upper section, the lower section having a top end and a bottom end,
wherein the top end of the lower section is adjacent the bottom of the deforming wall face, and
wherein a step portion is defined at the bottom end of the lower section, the step portion being adapted to contact a horizontal supporting plate at an opening formed through the horizontal supporting plate;
wherein said non-deforming section has:
a thick tube section that communicates with said deforming section and that is connected to the step portion of the lower section;
a thin tube section having said opening section; and
a transitional section formed between said thick tube section and said thin tube section,
wherein the non-deforming section is adapted to extend from the bottom end of the deforming section;
wherein the non-deforming section does not extend into the upper section that is deformable and thus the upper section and the non-deforming section are not radially overlapping;
wherein the lower section, which defines the step portion, is positioned between the non-deforming section and the upper section that is deformable so that the upper section is in communication with the non-deforming section via the lower section only; and wherein said thick tube section, said deforming section, and said transitional section are integrally formed, and a top end section of said thin tube section is fitted to a bottom end section of said transitional section, and attached by bonding or welding, and said thin tube section is formed from a member that is harder than said thick tube section, said deforming section, and said transitional section;

a dispensing head that supports one or two or more of the bellows type dispensing tips so that said opening section does not move due to deformation of said deforming wall face, and that performs suction/discharge of the liquid into or from said bellows type dispensing tip at once, by deforming said deforming wall face of said bellows type dispensing tip at once, a container set having a plurality of containers capable of accommodating various kinds of liquid solutions, and a head moving section that relatively moves said dispensing head with respect to said container set, and having a control section that controls deformation of said deforming wall face and/or movement between said dispensing head and the container set, based on the number or structure of said bellows type dispensing tip, a liquid to be suctioned/discharged, a substance contained in the liquid, an amount, an accommodating position, a temperature or concentration of the liquid, processing contents, or instructions.

10. A method of bellows type dispensing processing comprising:

a supporting step for supporting two or more bellows type dispensing tips having; an accommodating section that is capable of accommodating a liquid or gas in the interior thereof surrounded by a wall face, and that has a deforming wall face in a portion of said wall face, capable of a predetermined deformation without practically changing a total internal surface area of the wall face, and an opening section that is communicated with said accommodating section and that enables inflow and outflow of a liquid suctioned/discharged by expansion and contraction of said interior caused by deformation of the deforming wall face, on a dispensing head so that said opening section does not move due to deformation of said deforming wall face;

wherein the opening section can be inserted into a container capable of accommodating various kinds of liquid solutions;

wherein said opening section is provided at a bottom end of the bellows type dispensing tip; said deforming wall face is provided in a portion of a wall face surrounding said accommodating section so as to be able to deform in the vertical direction; said accommodating section has; a deforming section capable of accommodating a gas, that is provided above said opening section, and that has said deforming wall face, and a non-deforming section capable of accommodating a liquid, that communicates with said deforming section, that does not have said deforming wall face, and that has said opening section;

wherein said deforming section comprises:
an upper section that is deformable, the upper section comprising:
the deforming wall face that is adapted to be deformed to contract or expand the interior, the deforming wall face having a top and a bottom, and
a top end face adjacent the top of the deforming wall face,
wherein the top end face is adapted to contact a movable member; and
a lower section that is not deformable, the lower section being in communication with the upper section, the lower section having a top end and a bottom end,
wherein the top end of the lower section is adjacent the bottom of the deforming wall face, and
wherein a step portion is defined at the bottom end of the lower section, the step portion being adapted to contact a horizontal supporting plate at an opening formed through the horizontal supporting plate;

wherein said non-deforming section has:
a thick tube section that communicates with said deforming section and that is connected to the step portion of the lower section;
a thin tube section having said opening section; and
a transitional section formed between said thick tube section and said thin tube section, wherein the non-deforming section is adapted to extend from the bottom end of the deforming section;

wherein the non-deforming section does not extend into the upper section that is deformable and thus the upper section and the non-deforming section are not radially overlapping;

wherein the lower section, which defines the step portion, is positioned between the non-deforming section and the upper section that is deformable so that the upper section is in communication with the non-deforming section via the lower section only; and wherein said thick tube section, said deforming section, and said transitional section are integrally formed, and a top end section of said thin tube section is fitted to a bottom end section of said transitional section, and attached by bonding or welding, and said thin tube section is formed from a member that is harder than said thick tube section, said deforming section, and said transitional section;

a moving step for relatively moving said dispensing head with respect to said container set; and a deforming step for inserting said opening section into a container of the container set and deforming said deforming wall face at once, and in said deforming step and said moving step, deformation of said deforming wall face and/or movement between said dispensing head and the container set, is controlled based on the number or structure of said bellows type dispensing tip, a liquid to be suctioned/discharged, a substance contained in the liquid, an amount, an accommodating position, a temperature or concentration of the liquid, processing contents, or instructions.

* * * * *